United States Patent [19]

Skidmore et al.

[11] Patent Number: 4,943,591
[45] Date of Patent: Jul. 24, 1990

[54] DICHLOROANILINE DERIVATIVES

[75] Inventors: Ian F. Skidmore, Welwyn; Lawrence H. C. Lunts, Broxbourne; Harry Finch, Hitchin; Alan Naylor, Royston; Ian B. Campbell, The Blanes, all of England

[73] Assignee: Glaxo Group Limited, London, England

[21] Appl. No.: 918,317

[22] Filed: Oct. 14, 1986

Related U.S. Application Data

[63] Continuation-in-part of Ser. No. 788,122, Oct. 16, 1985, abandoned.

[30] Foreign Application Priority Data

Oct. 17, 1984 [GB] United Kingdom ................ 8426191
Oct. 15, 1985 [GB] United Kingdom ................ 8525321

[51] Int. Cl.$^5$ ............................................. A61K 31/13
[52] U.S. Cl. .................................. 514/539; 514/568; 514/630; 514/651; 562/430; 562/439; 562/452; 562/444; 562/448; 560/13; 560/22; 560/29; 560/42; 560/27; 560/34; 546/232; 546/233; 546/226; 548/556; 548/567; 548/569; 544/59; 544/159; 544/165; 544/398; 544/400; 549/441; 549/443; 549/365; 549/444; 558/408; 558/413; 558/414; 558/442; 564/50; 564/51; 564/56; 564/79; 564/99; 564/220; 564/221; 564/223; 564/165
[58] Field of Search ............... 514/630, 651, 539, 568; 564/220, 221; 560/22; 562/448, 444

[56] References Cited

U.S. PATENT DOCUMENTS

| | | | |
|---|---|---|---|
| 3,786,090 | 1/1974 | Hussain ........................... | 564/221 |
| 3,944,611 | 3/1976 | Smith .............................. | 564/220 |
| 3,993,780 | 11/1976 | Nakao et al. ..................... | 514/630 |
| 4,146,638 | 3/1979 | Renth et al. ..................... | 564/220 |
| 4,396,627 | 8/1983 | Ainsworth et al. .............. | 564/220 |
| 4,404,222 | 9/1983 | Báker et al. ..................... | 514/228 |
| 4,407,819 | 10/1983 | Kiernan et al. .................. | 514/376 |

FOREIGN PATENT DOCUMENTS

| | | |
|---|---|---|
| 0037781 | 10/1981 | European Pat. Off. ............ 514/651 |
| 199446A3 | 3/1985 | European Pat. Off. . |
| 3221540A1 | 12/1983 | Fed. Rep. of Germany . |
| 2210414 | 12/1974 | France . |
| 1178191 | 1/1970 | United Kingdom . |
| 2088873A | 6/1982 | United Kingdom . |

Primary Examiner—Glennon H. Hollrah
Assistant Examiner—Amelia A. Owens
Attorney, Agent, or Firm—Morgan & Finnegan

[57] ABSTRACT

The invention provides compounds of the general formula (I)

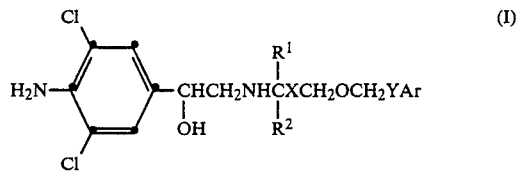

wherein
X represents a $C_{1-6}$ alkylene, $C_{2-6}$ alkenylene or $C_{2-6}$ alkynylene chain and
Y represents a bond, or a $C_{1-4}$ alkylene, $C_{2-4}$ alkenylene or $C_{2-4}$ alkynylene chain with the proviso that the sum total of carbon atoms in X and Y is not more than 8;
Ar represents a phenyl group optionally substituted by one or more substituents selected from halogen atoms or the groups $C_{1-3}$ alkyl, nitro, —$(CH_2)_qR$ [where R is hydroxy, $C_{1-3}$ alkoxy, —$NR^3R^4$ (where $R^3$ and $R^4$ each represent a hydrogen atom, or a $C_{1-4}$ alkyl group, or —$NR^3R^4$ forms a saturated heterocyclic amino group which has 5–7 ring members and optionally contains in the ring one or more atoms selected from —O— or —S— or a group —NH— or —N(CH_3)—), —$NR^5COR^6$ (where $R^5$ represents a hydrogen atom or a $C_{1-4}$ alkyl group, and $R^6$ represents a hydrogen atom or a $C_{1-4}$ alkyl, $C_{1-4}$ alkoxy or —$NR^3R^4$ group), and q represents an integer from 0 to 3], —$NR^5COR^{19}$ (where $R^5$ is as defined above and $R^{19}$ represents a phenyl group), —$(CH_2)_rR^7$ [where $R^7$ represents —$NR^5SO_2R^8$ (where $R^8$ represents a $C_{1-4}$ alkyl, phenyl or —$NR^3R^4$ group), —$NR^5COCH_2N(R^5)_2$ (where each of the groups $R^5$ represents a hydrogen atom or a $C_{1-4}$ alkyl group), —$COR^9$ (where $R^9$ represents hydroxy, $C_{1-4}$ alkoxy or $NR^3R^4$), —$SR^{10}$ (where $R^{10}$ is a hydrogen atom, or a $C_{1-4}$ alkyl group optionally substituted by hydroxy, $C_{1-4}$ alkoxy or $NR^3R^4$), —$SOR^{10}$, —$SO_2R^{10}$, —CN, or —$NR^{11}R^{12}$ (where $R^{11}$ and $R^{12}$ represent a hydrogen atom or a $C_{1-4}$ alkyl group, at least one of which is $C_{2-4}$alkyl substituted by a hydroxy, $C_{1-4}$ alkoxy or $NR^3R^4$), and r represents an integer from 0 to 3], —$O(CH_2)_qCOR^9$ (where q and $R^9$ are as defined above), or —$O(CH_2)_tR^{13}$ [where $R^{13}$ represents hydroxy, $NR^3R^4$, $NR^{11}R^{12}$ or a $C_{1-4}$ alkoxy group optionally substituted by hydroxy, $C_{1-4}$ alkoxy or $NR^3R^4$, and t is an integer 2 or 3], or Ar is a phenyl group substituted by an alkylenedioxy group —$O(CH_2)_pO$— where p is 1 or 2;
$R^1$ and $R^2$ each represents a hydrogen atom or a $C_{1-3}$ alkyl group, with the proviso that the sum total of carbon atoms in $R^1$ and $R^2$ is not more than 4;
and physiologically acceptable salts and solvates (e.g. hydrates) thereof.

The compounds of formula (I) have a stimulant action at $\beta_2$-adrenoreceptors and are useful, in particular, in the treatment of diseases associated with reversible airways obstruction such as asthma and chronic bronchitis.

8 Claims, No Drawings 4,943,591

DICHLOROANILINE DERIVATIVES

This is a continuation-in-part application of copending U.S. application Ser. No. 788,122, filed Oct. 16, 1985 now abandoned.

This invention relates to dichloroaniline derivatives having a stimulant action at $\beta_2$-adrenoreceptors, to processes for their preparation, to pharmaceutical compositions containing them and to their use in medicine.

Dihaloaniline derivatives have previously been described as bronchodilators having stimulant activity at $\beta$-adrenoreceptors.

Thus British Patent Specification No. 1178191 describes compounds of the general structure

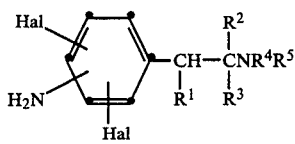

in which the substituents Hal represent bromine or chlorine atoms; $R^1$ represents hydrogen or hydroxyl; $R^2$ and $R^3$ each represent hydrogen or $C_{1-4}$ alkyl; and $R^4$ and $R^5$ each represent hydrogen, $C_{1-6}$ alkyl, alkenyl, alkynyl, hydroxyalkyl, alkoxyalkyl, dialkylaminoalkyl, cycloalkyl, phenyl, benzyl or adamantyl, or $NR^4R^5$ forms a heterocylic ring optionally substituted by $C_{1-3}$ alkyl groups.

We have now found a novel group of dichloroaniline derivatives, which differ structurally from those described in British Patent Specification No. 1178191, and which have a desirable and useful profile of activity.

Thus the present invention provides compounds of the general formula (I)

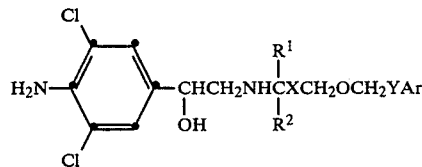

wherein

X represents a $C_{1-6}$ alkylene, $C_{2-6}$ alkenylene or $C_{2-6}$ alkynylene chain and Y represents a bond, or a $C_{1-4}$ alkylene, $C_{2-4}$ alkenylene or $C_{2-4}$ alkynylene chain with the proviso that the sum total of carbon atoms in X and Y is not more than 8;

Ar represents a phenyl group optionally substituted by one or more substituents selected from halogen atoms or the groups $C_{1-3}$ alkyl, nitro, —$(CH_2)qR$ [where R is hydroxy, $C_{1-3}$ alkoxy, —$NR^3R^4$ (where $R^3$ and $R^4$ each represent a hydrogen atom, or a $C_{1-4}$ alkyl group, or —$NR^3R^4$ forms a saturated heterocyclic amino group which has 5-7 ring members and optionally contains in the ring one or more atoms selected from —O— or —S— or a group —NH— or —N(CH$_3$)—), —$NR^5COR^6$ (where $R^5$ represents a hydrogen atom or a $C_{1-4}$ alkyl group, and $R^6$ represents a hydrogen atom or a $C_{1-4}$ alkyl, $C_{1-4}$ alkoxy or —$NR^3R^4$ group), and q represents an integer from 0 to 3], —$NR^5COR^{19}$ (where $R^5$ is as defined above and $R^{19}$ represents a phenyl group), —$(CH_2)_rR^7$ [where $R^7$ represents —$NR^5SO_2R^8$ (where $R^8$ represents a $C_{1-4}$ alkyl, phenyl or —$NR^3R^4$ group), —$NR^5COCH_2N(R^5)_2$ (where each of the groups $R^5$ represents a hydrogen atom or a $C_{1-4}$ alkyl group), —$COR^9$ (where $R^9$ represents hydroxy, $C_{1-4}$ alkoxy or $NR^3R^4$), —$SR^{10}$ (where $R^{10}$ is a hydrogen atom, or a $C_{1-4}$ alkyl group optionally substituted by hydroxy, $C_{1-4}$ alkoxy or $NR^3R^4$), —$SOR^{10}$, —$SO_2R^{10}$, —CN, or —$NR^{11}R^{12}$ (where $R^{11}$ and $R^{12}$ represent a hydrogen atom or a $C_{1-4}$ alkyl group, at least one of which is $C_{2-4}$alkyl substituted by a hydroxy, $C_{1-4}$ alkoxy or $NR^3R^4$ group), and r represents an integer from 0 to 3], —$O(CH_2)_qCOR^9$ (where q and $R^9$ are as defined above), or —$O(CH_2)_tR^{13}$ [where $R^{13}$ represents hydroxy, $NR^3R^4$, $NR^{11}R^{12}$ or a $C_{1-4}$ alkoxy group optionally substituted by hydroxy, $C_{1-4}$ alkoxy or $NR^3R^4$, and t is an integer 2 or 3], or Ar is a phenyl group substituted by an alkylenedioxy group —$O(CH_2)_pO$— where p is 1 or 2;

$R^1$ and $R^2$ each represents a hydrogen atom or a $C_{1-3}$ alkyl group, with the proviso that the sum total of carbon atoms in $R^1$ and $R^2$ is not more than 4; and physiologically acceptable salts and solvates (e.g. hydrates) thereof.

It will be appreciated that the compounds of general formula (I) possess one or two asymmetric carbon atoms, namely the carbon atom of the

group and, when $R^1$ and $R^2$ are different groups, the carbon atom to which these are attached.

The compounds according to the invention thus include all enantiomers, diastereoisomers and mixtures thereof, including racemates. Compounds in which the carbon atom in the

group is in the R configuration are preferred.

In the definition of general formula (I), the term alkenylene includes both cis and trans structures.

In one aspect, the invention provides compounds of formula (I) in which $R^1$, $R^2$, and Y are as defined in formula (I), X represents a $C_{2-6}$ alkylene, $C_{2-6}$ alkenylene or $C_{2-6}$ alkynylene chain, and Ar represents a phenyl group optionally substituted by one or more substituents selected from halogen atoms or the groups $C_{1-3}$ alkyl, —$(CH_2)_qOH$ (where q is an integer from 0 to 3), $C_{1-3}$ alkoxy, —$NR^3R^4$ (where $R^3$ and $R^4$ are as defined in formula I), or —$NR^5COR^6$ or —$NR^5COR^{19}$ (where $R^5$, $R^6$ and $R^{19}$ are as defined in formula I), or Ar is a phenyl group substituted by the group —$O(CH_2)_pO$— as defined in formula (I).

In another aspect the invention provides compounds of formula (I) in which $R^1$, $R^2$, X and Y are as defined in formula (I), and Ar represents a phenyl group substituted by one or more substituents selected from the groups nitro, —$(CH_2)_qR$ [where R is $C_{1-3}$ alkoxy, —$NR^3R^4$ or —$NR^5COR^6$ (where $R^3$, $R^4$, $R^5$ and $R^6$ are as defined in formula I), and q is an integer from 1 to 3], —$(CH_2)_rR^7$ [where $R^7$ represents —$NR^5SO_2R^8$, —COR$^9$, —SR$^{10}$, —SOR$^{10}$, —SO$_2$R$^{10}$, —CN or —NR$^{11}$R$^{12}$ (where r, R$^5$, R$^8$, R$^9$, R$^{10}$, R$^{11}$ and R$^{12}$ are as defined in formula I)], —O(CH$_2$)$_q$COR$^9$ or —O(CH$_2$)$_t$R$^{13}$ (where R$^9$, R$^{13}$, q and t are as defined in formula I).

In the general formula (I), the chain X may be for example —CH$_2$—, —(CH$_2$)$_2$—, —(CH$_2$)$_3$—, —(CH$_2$)$_4$—, —(CH$_2$)$_5$—, —(CH$_2$)$_6$—, —CH$_2$C≡C—, —(CH$_2$)$_2$CH=CH—, —(CH$_2$)$_2$C≡C—, —CH=CHCH$_2$—, —CH=CH(CH$_2$)$_2$— or —CH$_2$C≡CCH$_2$—. The chain Y may be for example a bond, —CH$_2$—, —(CH$_2$)$_2$—, —(CH$_2$)$_3$—, —(CH$_2$)$_4$—, —CH=CH—, —C≡C—, CH$_2$CH=CH—, or —CH$_2$C≡C—.

Preferably the total number of carbon atoms in the chains X and Y is 4 to 8 inclusive. Compounds wherein the sum total of carbon atoms in the chains X and Y is 4, 5, 6 or 7 are particularly preferred.

In one preferred group of compounds of formula (I) X represents a C$_{2-6}$ alkynylene or, more preferably, a C$_{2-6}$ alkylene chain and Y represents a C$_{1-4}$ alkylene chain. Particular compounds of this type are those wherein X is —(CH$_2$)$_3$— or —(CH$_2$)$_4$— and Y is —CH$_2$—, —(CH$_2$)$_2$— or —(CH$_2$)$_3$—, or X is —CH$_2$C≡C— and Y is —CH$_2$—.

In the compounds of formula (I) R$^1$ and R$^2$ may each be, for example, methyl, ethyl, propyl or isopropyl groups except that if one of R$^1$ and R$^2$ is a propyl or isopropyl group, the other is a hydrogen atom or a methyl group. Thus for example R$^1$ may be a hydrogen atom or a methyl, ethyl or propyl group. R$^2$ may be, for example, a hydrogen atom or a methyl group. R$^1$ and R$^2$ are each preferably a hydrogen atom or a methyl group.

A preferred group of compounds are those wherein R$^1$ and R$^2$ are both hydrogen atoms, or R$^1$ is a hydrogen atom and R$^2$ is a C$_{1-3}$ alkyl group, particularly a methyl group.

When —NR$^3$R$^4$ in compounds of formula (I) represents a saturated heterocyclic amino group, this may have 5, 6 or 7 ring members and optionally contains in the ring a heteroatom selected from —O— or —S—, or a group —NH— or —N(CH$_3$)—. Examples of such —NR$^3$R$^4$ groups are pyrrolidino, piperidino, hexamethyleneimino, piperazino, N-methylpiperazino, morpholino, homomorpholino or thiamorpholino.

Ar may be for example a phenyl group. Examples of the optional substituents which may be present on the phenyl group represented by Ar include bromine, iodine, chlorine, fluorine, methyl, ethyl, methoxy, ethoxy, amino, methylamino, ethylamino, dimethylamino, diethylamino, morpholino, piperidino, piperazino, N-methylpiperazino, —NHCOR$^6$ [where R$^6$ is hydrogen, C$_{1-4}$ alkyl, (e.g. methyl, ethyl, isopropyl or n-butyl), C$_{1-4}$ alkoxy (e.g. methoxy, ethoxy, isopropoxy or n-butoxy), phenyl or amino], hydroxyl, —CH$_2$OH, —(CH$_2$)$_2$OH, —(CH$_2$)$_q$R [where R represents C$_{1-3}$ alkoxy e.g. methoxy, diC$_{1-4}$alkylamino e.g. dimethylamino, morpholino, piperidino, piperazino, N-methylpiperazino, —NHCOR$^6$ (where R$^6$ is C$_{1-4}$ alkyl e.g. methyl), and q is 1 or 2], —(CH$_2$)$_r$R$^7$ [where R$^7$ represents —NR$^5$SO$_2$R$^8$ (where R$^5$ represents hydrogen or methyl, and R$^8$ represents C$_{1-4}$ alkyl e.g. methyl), —NHCOCH$_2$N(R$^5$)$_2$ (where both groups R$^5$ represent C$_{1-4}$ alkyl e.g. methyl), —COR$^9$ (where R$^9$ represents C$_{1-4}$ alkoxy e.g. ethoxy, amino, diC$_{1-4}$alkylamino e.g. dimethylamino, morpholino, piperidino, piperazino or N-methylpiperazino), —NR$^{11}$R$^{12}$ (where one or both of R$^{11}$ and R$^{12}$ represents a C$_{2-4}$ alkyl e.g. ethyl group substituted by a hydroxy or diC$_{1-4}$alkylamino e.g. dimethylamino group, and the other represents a hydrogen atom), and r is zero or 1], —OCH$_2$COR$^9$ (where R$^9$ is diC$_{1-4}$alkylamino e.g. dimethylamino), or —O(CH$_2$)$_2$R$^{13}$ (where R$^{13}$ is diC$_{1-4}$alkylamino e.g. dimethylamino).

The phenyl group represented by Ar may optionally contain one, two or three substituents, which may be present at the 2-, 3-, 4-, 5- or 6-positions on the phenyl ring.

Particular examples of a disubstituted phenyl group represented by Ar include phenyl substituted by two hydroxyl groups [e.g. 3,5-dihydroxyphenyl], or a hydroxyl and a methoxy group [e.g. 3-methoxy-4-hydroxyphenyl].

Particular examples of a trisubstituted phenyl group represented by Ar include phenyl substituted by an amino and two methyl groups [e.g. 3,5-dimethyl-4-aminophenyl], an amino group and two chlorine atoms [e.g. 3,5-dichloro-4-aminophenyl], or three methoxy groups [e.g. 3,4,5-trimethoxyphenyl].

A preferred group of compounds are those of the formula (Ia)

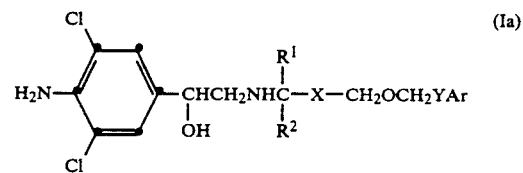

(Ia)

wherein
X represents a C$_{3-4}$ alkylene or C$_3$ alkynylene chain;
Y represents a C$_{1-3}$ alkylene chain;
R$^1$ and R$^2$ each represent hydrogen or methyl; and
Ar represents a phenyl group optionally substituted by a fluorine atom, a group selected from amino, C$_{1-3}$ alkyl (e.g. methyl), C$_{1-3}$ alkoxy (e.g. methoxy), hydroxy C$_{1-2}$ alkyl (e.g. hydroxymethyl), morpholino, hydroxy or —NHCOR$^6$ where R$^6$ is C$_{1-3}$ alkyl (e.g. methyl), or Ar is a phenyl group substituted by hydroxyl groups at the 3- and 5-positions; and physiologically acceptable salts and solvates thereof.

A particularly preferred group of compounds of formula (Ia) are those wherein Ar is a phenyl group optionally containing one substituent, more preferably an amino, —NHAcetyl or morpholino group.

A further preferred group of compounds according to the invention are those of the formula (Ib)

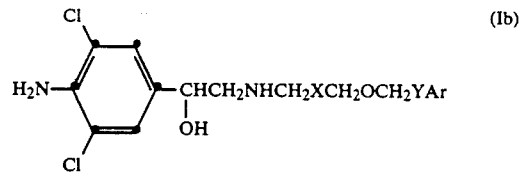

(Ib)

wherein X represents a C$_{3-4}$ alkylene chain and Y represents a C$_{1-3}$ alkylene chain with the proviso that the total number of carbon atoms in X and Y is 5 or 6; and Ar represents a phenyl group substituted by a group selected from C$_{1-4}$ alkoxymethyl (e.g. methoxymethyl), morpholinomethyl, diC$_{1-4}$alkylaminoC$_{1-2}$alkyl (e.g. dimethylaminoethyl), —CH$_2$NHCOR$^6$ (where R$^6$ is C$_{1-4}$ alkyl e.g. methyl), —NR$^5$SO$_2$R$^8$ (where R$^5$ is hydrogen or methyl and $R^8$ is $C_{1-4}$ alkyl e.g. methyl), —NHCOCH$_2$N(R$^5$)$_2$ (where both groups $R^5$ represent $C_{1-4}$ alkyl e.g. methyl), —COR$^9$ (where $R^9$ is hydroxy, $C_{1-4}$ alkoxy e.g. ethoxy, amino, diC$_{1-4}$alkylamino e.g. dimethylamino, or morpholino), —CH$_2$COR$^9$ (where $R^9$ is amino or diC$_{1-4}$alkylamino e.g. dimethylamino), —NR$^{11}$R$^{12}$ (where R$^{11}$ and R$^{12}$ both represent hydroxy $C_{2-4}$ alkyl e.g. hydroxyethyl), diC$_{1-4}$alkylaminoethylamino (e.g. dimethylaminoethylamino), —OCH$_2$COR$^9$ (where $R^9$ is diC$_{1-4}$alkylamino e.g. dimethylamino) or —O(CH$_2$)$_2$R$^{13}$ (where R$^{13}$ is diC$_{1-4}$alkylamino e.g. dimethylamino); and physiologically acceptable salts and solvates thereof.

Particularly preferred compounds of formula (Ib) are those in which X and Y are as defined for formula (Ib); and Ar represents a phenyl group substituted by a group selected from —CH$_2$NHCOR$^6$ (where R$^6$ is methyl), —NHSO$_2$R$^8$ (where R$^8$ is methyl), —COR$^9$ (where R$^9$ is hydroxy, ethoxy, amino or morpholino), or —CH$_2$COR$^9$ (where R$^9$ is amino or dimethylamino), and physiologically acceptable salts and solvates thereof.

Particularly important compounds of the invention are:

4-amino-3,5-dichloro-α-[[[6-[2-[4-(4-morpholinyl)-phenyl]ethoxy]hexyl]amino]methyl]benzenemethanol;
N-[4-[2-[[6-[[2-(4-amino-3,5-dichlorophenyl)-2-hydroxyethyl]amino]hexyl]oxy]ethyl]phenyl]acetamide;
4-amino-3,5-dichloro-α-[[[6-[2-(4-aminophenyl)ethoxy]-hexyl]amino]methyl]benzenemethanol;
4-amino-3,5-dichloro-α-[[[5-(2-phenylethoxy]pentyl]amino]methyl]benzenemethanol;
4-amino-3,5-dichloro-α-[[[6-(2-phenylethoxy)hexyl]amino]methyl]benzenemethanol;
4-amino-3,5-dichloro-α-[[[1-methyl-5-(2-phenylethoxy)pentyl]amino]methyl]benzenemethanol;
4-amino-3,5-dichloro-α-[[[5-(2-phenylethoxy)-3-pentynyl]amino]methyl]benzenemethanol;
[3-[[5-[[2-(4-amino-3,5-dichlorophenyl)-2-hydroxyethyl]amino]pentyl]oxy]propyl]-1,3-benzenediol;
4-amino-3,5-dichloro-α-[[[5-[2-(4-methoxyphenyl)ethoxy]pentyl]amino]methyl]benzenemethanol;
4-[3-[[6-[[2-(4-amino-3,5-dichlorophenyl)-2-hydroxyethyl]amino]hexyl]oxy]propyl]benzamide;
ethyl 4-[3-[[6-[[(4-amino-3,5-dichlorophenyl)-2-hydroxyethyl]amino]hexyl]oxy]propyl]benzoate;
N-[[3-[3-[[6-[[2-(4-amino-3,5-dichlorophenyl)-2-hydroxyethyl]amino]hexyl]oxy]propyl]phenyl]methyl]acetamide;
4-[4-[5-[[2-(4-amino-3,5-dichlorophenyl)-2-hydroxyethyl]amino]pentyloxy]butyl]-N,N-dimethyl benzeneacetamide acetamide;
4-[3-[[6-[[2-(4-amino-3,5-dichlorophenyl)-2-hydroxyethyl]amino]hexyl]oxy]propylbenzoic acid;
4-[4-[3-[[6-[[2-(4-amino-3,5-dichlorophenyl)-2-hydroxyethyl]amino]hexyl]oxy]propyl]benzoyl]morpholine;
N-[4-[3-[[6-[[2-(4-amino-3,5-dichlorophenyl)-2-hydroxyethyl]amino]hexyl]oxy]ethyl]phenyl]methanesulphonamide;
[4-[3-[[6-[[2-(4-amino-3,5-dichlorophenyl)-2-hydroxyethyl]amino]hexyl]oxy]propyl]benzeneacetamide;
and the physiologically acceptable salts and solvates thereof.

Suitable physiologically acceptable salts of the compounds of general formula (I) include acid addition salts derived from inorganic and organic acids, such as hydrochlorides, hydrobromides, sulphates, phosphates, maleates, tartrates, citrates, benzoates, 4-methoxybenzoates, 2- or 4-hydroxybenzoates, 4-chlorobenzoates, p-toluenesulphonates, methanesulphonates, sulphamates, ascorbates, salicylates, acetates, fumarates, succinates, lactates, glutarates, gluconates, tricarballylates, hydroxy-naphthalenecarboxylates e.g. 1-hydroxy- or 3-hydroxy-2-naphthalenecarboxylates, or oleates. The compounds may also form salts with suitable bases. Examples of such salts are alkali metal (e.g. sodium and potassium), and alkaline earth metal (e.g. calcium or magnesium) salts.

The compounds according to the invention have a stimulant action at $\beta_2$-adrenoreceptors, which furthermore is of a particularly advantageous profile. The stimulant action was demonstrated in the isolated trachea of the guinea-pig, where compounds were shown to cause relaxation of PGF2α-induced contractions. Compounds according to the invention have shown a particularly long duration of action in this test.

The compounds according to the invention may be used in the treatment of diseases associated with reversible airways obstruction such as asthma and chronic bronchitis.

The compounds according to the invention are also indicated as useful for the treatment of inflammatory and allergic skin diseases, congestive heart failure, depression, premature labour, glaucoma, and in the treatment of conditions in which there is an advantage in lowering gastric acidity, particularly in gastric and peptic ulceration.

The invention accordingly further provides compounds of formula (I) and their physiologically acceptable salts and solvates for use in the therapy or prophylaxis of diseases associated with reversible airways obstruction in human or animal subjects.

The compounds according to the invention may be formulated for administration in any convenient way. The invention therefore includes within its scope pharmaceutical compositions comprising at least one compound of formula (I) or a physiologically acceptable salt or solvate thereof formulated for use in human or veterinary medicine. Such compositions may be presented for use with physiologically acceptable carriers or excipients, optionally with supplementary medicinal agents.

The compounds may be formulated in a form suitable for administration by inhalation or insufflation, or for oral, buccal, parenteral, topical (including nasal) or rectal administration. Administration by inhalation or insufflation is preferred.

For administration by inhalation the compounds according to the invention are conveniently delivered in the form of an aerosol spray presentation from pressurised packs, with the use of a suitable propellant, such as dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in for example capsules or cartridges of e.g. gelatin, or blister packs from which the powder may be administered with the aid of an inhaler or insufflator.

For oral administration, the pharmaceutical composition may take the form of, for example, tablets, capsules, powders, solutions, syrups or suspensions prepared by conventional means with acceptable excipients.

For buccal administration the composition may take the form of tablets, drops or lozenges formulated in conventional manner.

The compounds of the invention may be formulated for parenteral administration by bolus injection or continuous infusion. Formulations for injection may be presented in unit dosage form in ampoules, or in multi-dose containers with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water, before use.

For topical administration the pharmaceutical composition may take the form of ointments, lotions or creams formulated in a conventional manner, with for example an aqueous or oily base, generally with the addition of suitable thickening agents and/or solvents. For nasal application, the composition may take the form of a spray, formulated for example as an aqueous solution or suspension or as an aerosol with the use of a suitable propellant.

The compounds of the invention may also be formulated in rectal compositions such as suppositories or retention enemas, e.g. containing conventional suppository bases such as cocoa butter or other glyceride.

Where pharmaceutical compositions are described above for oral, buccal, rectal or topical administration, these may be presented in a conventional manner associated with controlled release forms.

A proposed daily dosage of active compound for the treatment of man is 0.005 mg to 100 mg, which may be conveniently administered in one or two doses. The precise dose employed will of course depend on the age and condition of the patient and on the route of administration. Thus a suitable dose for administration by inhalation is 0.005 mg to 20 mg, for oral administration is 0.02 mg to 100 mg, and for parenteral administration is 0.01 mg to 2 mg for administration by bolus injection and 0.01 mg to 25 mg for administration by infusion.

The compounds according to the invention may be prepared by a number of processes, as described in the following wherein X, Y, Ar, $R^1$ and $R^2$ are as defined for general formula (I) unless otherwise specified. In addition, any substituent in the group Ar may be a precursor substituent which is convertible into the required substituent by conventional methods.

It will be appreciated that certain of the reactions described below are capable of affecting other groups in the starting material which are desired in the end product; this applies especially in the reduction processes described, particularly where hydrogen and a catalyst are used and when an ethylene or acetylene linkage is required in the compound of the invention. Care must therefore be taken in accordance with conventional practice, either to use reagents which will not affect such groups, or to perform the reaction as part of a sequence which avoids their use when such groups are present in the starting material.

In the preparation of both intermediates and end-products the final step in the reaction may be the removal of a protecting group. Conventional protecting groups may be used, as described for example in "Protective Groups in Organic Chemistry", Ed. J. F. W. McOmie (Plenum Press, 1973). Thus hydroxyl groups may for example be protected by aralkyl groups such as benzyl, diphenylmethyl or triphenylmethyl, or as tetrahydropyranyl derivatives. Suitable amino protecting groups include aralkyl groups such as benzyl, α-methylbenzyl, diphenylmethyl or triphenylmethyl, and acyl groups such as acetyl, trichloroacetyl or trifluoroacetyl.

Conventional methods of deprotection may be used. Thus for example aralkyl groups may be removed by hydrogenolysis in the presence of a metal catalyst (e.g. palladium on charcoal). Tetrahydropyranyl groups may be cleaved by hydrolysis under acidic conditions. Acyl groups may be removed by hydrolysis with an acid such as a mineral acid e.g. hydrochloric acid, or a base such as sodium hydroxide or potassium carbonate, or a group such as trichloroacetyl may be removed by reduction with, for example, zinc and acetic acid.

In one general process (1), a compound of general formula (I) may be prepared by alkylation. Conventional alkylation procedures may be used.

Thus, for example, in one process (a), a compound of general formula (I) in which $R^1$ is a hydrogen atom may be prepared by alkylation of an amine of general formula (II)

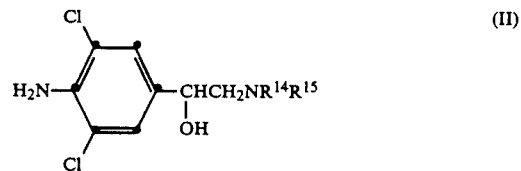
(II)

(wherein $R^{14}$ is a hydrogen atom or a protecting group and $R^{15}$ is a hydrogen atom) followed by removal of any protecting group where present.

The alkylation (a) may be effected using an alkylating agent of general formula (III):

(III)

(wherein L is a leaving group, for example a halogen atom such as chlorine, bromine or iodine, or a hydrocarbylsulphonyloxy group such as methanesulphonyloxy or p-toluenesulphonloxy).

The alkylation is preferably effected in the presence of a suitable acid scavenger, for example, inorganic bases such as sodium or potassium carbonate, organic bases such as triethylamine, diisopropylethylamine or pyridine, or alkylene oxides such as ethylene oxide or propylene oxide. The reaction is conveniently effected in a solvent such as acetonitrile or an ether e.g. tetrahydrofuran or dioxan, a ketone e.g. butanone or methyl isobutyl ketone, a substituted amide e.g. dimethylformamide or a chlorinated hydrocarbon e.g. chloroform at a temperature between ambient and the reflux temperature of the solvent.

According to another example (b) of an alkylation process, a compound of general formula (I) in which $R^1$ represents a hydrogen atom may be prepared by alkylation of an amine of general formula (II), as previously defined except that $R^{15}$ is a hydrogen atom or a group convertible thereto under the reaction conditions, with a compound of general formula (IV):

$$R^2COXCH_2OCH_2YAr \qquad (IV)$$

in the presence of a reducing agent, followed when necessary by removal of any protecting groups.

Examples of suitable $R^{15}$ groups convertible into a hydrogen atom are arylmethyl groups such as benzyl, α-methylbenzyl and benzhydryl.

Suitable reducing agents include hydrogen in the presence of a catalyst such as platinum, platinum oxide, palladium, palladium oxide, Raney nickel or rhodium, on a support such as charcoal, using an alcohol, e.g. ethanol or methanol, or an ester e.g. ethyl acetate, or an ether e.g. tetrahydrofuran, or water, as reaction solvent, or a mixture of solvents, e.g. a mixture of two or more of those just described at normal or elevated temperature and pressure, for example from 20° to 100° C. and from 1 to 10 atmospheres.

Alternatively when one or both of $R^{14}$ and $R^{15}$ are hydrogen atoms, the reducing agent may be a hydride such as diborane or a metal hydride such as sodium borohydride, sodium cyanoborohydride or lithium aluminium hydride. Suitable solvents for the reaction with these reducing agents will depend on the particular hydride used, but will include alcohols such as methanol or ethanol, or ethers such as diethyl ether or tert-butyl methyl ether, or tetrahydrofuran.

When a compound of formula (II) where $R^{14}$ and $R^{15}$ are each hydrogen atoms is used, the intermediate imine of formula (V) may be formed:

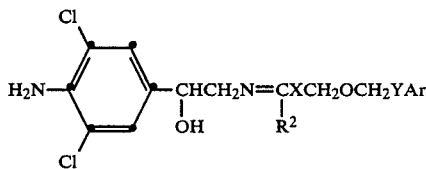

(V)

Reduction of the imine using the conditions described above, followed, where necessary, by removal of any protecting groups, gives a compound of general formula (I).

Where it is desired to use a protected intermediate of general formula (II) it is particularly convenient to use hydrogen and a catalyst as described above with protecting groups $R^{14}$ which are capable of being converted to a hydrogen atom under these reducing conditions, thus avoiding the need for a separate deprotection step. Suitable protecting groups of this type include arylmethyl groups such as benzyl, benzhydryl and α-methylbenzyl.

In another general process (2), a compound of general formula (I) may be prepared by reduction. Thus, for example, a compound of general formula (I) may be prepared by reducing an intermediate of general formula (VI):

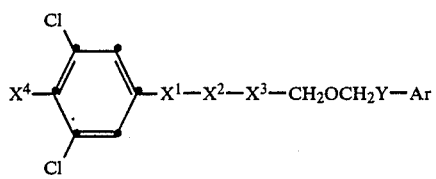

(VI)

wherein at least one of $X^4$, $X^1$, $X^2$, $X^3$ and Y represents a reducible group and/or Ar contains a reducible group and the other(s) take the appropriate meaning as follows, which is $X^4$ is $-NH_2$, $X^1$ is $-CH(OH)-$, $X^2$ is $-CH_2NR^{14}-$ (wherein $R^{14}$ is a hydrogen atom or a protecting group), $X^3$ is $-CR^1R^2X$, and Ar and Y are as defined in formula (I), followed where necessary by removal of any protecting groups.

Suitable reducible groups include those wherein $X^4$ is $-NO_2$, $X^1$ is a group $>C=O$, $X^2$ is a group $-CH_2NY'-$ (wherein Y' represents a group convertible to hydrogen by catalytic hydrogenation, for example an arylmethyl group such as benzyl, benzhydryl or α-methylbenzyl), or an imine ($-CH=N-$) group or a group $-CONH-$, $X^3$ is a group $-COX-$ or a group $CR^1R^2X$ (where X is $C_{2-6}$ alkenylene or $C_{2-6}$ alkynylene), or $-X^2-X^3-$ is a group $-CH_2N=CR^2X-$, Y is $C_{2-4}$ alkenylene or alkynylene, and Ar is a phenyl group substituted by a nitro group, or by a group containing an amide linkage such as $-(CH_2)_{q-1}CONR^3R^4$ or $-NHCOR^{17}$ (where $-NHCOR^{17}$ is reducible to the group $NHR^{12}$), or by a group $-CHO$ or $-CO_2R^{18}$ (where $R^{18}$ is hydrogen or an alkyl e.g. $C_{1-3}$ alkyl group).

The reduction may be effected using reducing agents conveniently employed for the reduction of carboxylic acids, aldehydes, esters, ketones, imines, amides, protected amines, alkenes, alkynes and nitro groups. Thus, for example, when $X^4$ in general formula (VI) represents a nitro group or the phenyl group Ar contains a nitro substituent, this may be reduced to an amino group using hydrogen in the presence of a catalyst as previously described for process (1) part (b).

When $X^1$ in general formula (VI) represents a $>C=O$ group this may be reduced to a $-CH(OH)-$ group using hydrogen in the presence of a catalyst as previously described for process (1) part (b). Alternatively, the reducing agent may be, for example, a hydride such as diborane or a metal hydride such as lithium aluminium hydride, sodium bis(2-methoxyethoxy) aluminium hydride, sodium borohydride or aluminium hydride. The reaction may be effected in a solvent, where appropriate an alcohol e.g. methanol or ethanol, or an ether such as tetrahydrofuran, or a halogenated hydrocarbon such as dichloromethane.

When $X^2$ in general formula (VI) represents a $-CH_2NY'-$ group or the group $-CH=N-$, or $-X^2-X^3-$ represents $-CH_2N=CR^2X-$ this may be reduced to a $-CH_2NH-$ or $-CH_2NHCHR^2X-$ group using hydrogen in the presence of a metal catalyst as previously described for process (1) part (b). Alternatively, when $X^2$ or $-X^2-X^3-$ is the group $-CH=N-$ or $-CH_2N=CR^2X-$ this may be reduced to a $-CH_2NH-$ or $-CH_2NHCHR^2X-$ group using a reducing agent and conditions as just described for the reduction of $X^1$ when this represents a $>C=O$ group.

When $X^2$ or $X^3$ in general formula (VI) represents a $-CONH-$ or $-COX-$ group, or Ar is phenyl substituted by a group containing an amide linkage such as $-(CH_2)_{q-1}CONR^3R^4$ or $-NHCOR^{17}$ (where $R^{17}$ is as defined previously), this may be reduced to a group $-CH_2NH-$ or $-CH_2X-$, or to phenyl substituted by the group $-(CH_2)_qNR^3R^4$ or $-NHR^{12}$, respectively, using a hydride such as diborane or a complex metal hydride such as lithium aluminium hydride or sodium bis(2-methoxyethoxy)aluminium hydride in a solvent such as an ether, e.g. tetrahydrofuran or diethyl ether.

When $X^3$ represents a group $CR^1R^2X$ where X is $C_{2-6}$ alkenylene or $C_{2-6}$ alkynylene, or Y represents $C_{2-4}$ alkenylene or $C_{2-4}$ alkynylene, this may be reduced to $C_{2-6}$ alkylene or $C_{2-4}$ alkylene respectively using hydrogen in the presence of a catalyst as previously described for process (1) part (b). Alternatively, when X is $C_{2-6}$ alkynylene or Y is $C_{2-4}$ alkynylene this may be reduced to $C_{2-6}$ alkenylene or $C_{2-4}$ alkenylene respectively using for example hydrogen and a lead-poisoned palladium on calcium carbonate catalyst in a solvent such as pyridine, or lithium aluminium hydride in a solvent such as diethyl ether at a low temperature e.g. 0° C.

When Ar is phenyl substituted by a group —CHO or —$CO_2R^{18}$ (where $R^{18}$ is hydrogen or alkyl) this may be reduced to phenyl substituted by a hydroxymethyl group using for example a complex metal hydride such as lithium aluminium hydride or sodium borohydride.

In a further general process (3), a compound of general formula (I) may be prepared by deprotection of a protected intermediate of formula (VII)

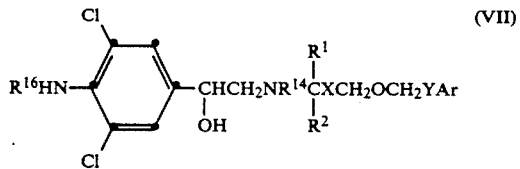

where $R^{14}$ and $R^{16}$ each represent a hydrogen atom or a protecting group, and/or any hydroxy and/or amino substituent in the group Ar is protected, with the proviso that at least one of $R^{14}$ and/or $R^{16}$ represents a protecting group and/or Ar contains a protecting group.

Suitable protecting groups and their methods of removal are as described previously. Thus, for example, $R^{14}$ may represent an aralkyl group e.g. benzyl, which may be removed by hydrogenolysis in the presence of a metal catalyst (e.g. palladium on charcoal), and/or $R^{16}$ may represent an acyl group which may be removed by boiling with a dilute mineral acid (e.g. hydrochloric acid).

Compounds of formula (I) may also be prepared by a process comprising interconversion of one compound of general formula (I) to another.

Thus for example a compound of formula (I) in which Ar represents a phenyl group substituted by the group —$(CH_2)_rCOR^9$ where $R^9$ is hydroxy may be prepared by hydrolysis of the corresponding compound of formula (I) in which $R^9$ represents $C_{1-4}$ alkoxy. The hydrolysis may for example be carried out under basic conditions using e.g. sodium hydroxide.

In the general processes described above, the compound of formula (I) obtained may be in the form of a salt, conveniently in the form of a physiologically acceptable salt. Where desired, such salts may be converted to the corresponding free acids using conventional methods.

Physiologically acceptable salts of the compounds of general formula (I) may be prepared by reacting a compound of general formula (I) with an appropriate acid or base in the presence of a suitable solvent such as acetonitrile, acetone, chloroform, ethyl acetate or an alcohol, e.g. methanol, ethanol or iso-propanol.

Physiologically acceptable salts may also be prepared from other salts, including other physiologically acceptable salts, of the compounds of general formula (I), using conventional methods.

When a specific enantiomer of a compound of general formula (I) is required, this may be obtained by resolution of a corresponding racemate of a compound of general formula (I) using conventional methods.

Thus, in one example an appropriate optically active acid may be used to form salts with the racemate of a compound of general formula (I). The resulting mixture of isomeric salts may be separated for example by fractional crystallisation, into the diastereoisomeric salts from which the required enantiomer of a compound of general formula (I) may be isolated by conversion into the required free base.

Alternatively, enantiomers of a compound of general formula (I) may be synthesised from the appropriate optically active intermediates using any of the general processes described herein.

Specific diastereoisomers of a compound of formula (I) may be obtained by conventional methods for example, by synthesis from an appropriate asymmetric starting material using any of the processes described herein, or by conversion of a mixture of isomers of a compound of general formula (I) into appropriate diastereoisomeric derivatives e.g. salts which then can be separated by conventional means e.g. by fractional crystallisation.

Suitable methods for preparing the intermediate compounds used in the above general processes are described below. In the following discussion, Ar, $R^1$, $R^2$, $R^{14}$, $R^{15}$, X, $X^1$, $X^2$, $X^3$, $X^4$, Y, Y' and L are as defined above except where otherwise indicated. In addition, any substituent in the group Ar may be a precursor substituent which is convertible into the required substituent during the subsequent final-step process. "Hal" represents a halogen atom.

Intermediate compounds of general formula (VI) for use in general process (2) may be prepared by a number of processes.

Thus for example intermediates of general formula (VI) in which $X^1$ is a group —C=O may be prepared from a haloketone of formula (VIII)

by reaction with an amine of general formula (IX)

(wherein $Y^1$ is hydrogen or a group convertible thereto by catalytic hydrogenation). The reaction may be effected in a cold or hot solvent, for example tetrahydrofuran, tert-butyl methyl ether, dioxan, chloroform, dimethylformamide, acetonitrile or a ketone such as butanone or methylisobutylketone, or an ester, for example ethyl acetate, preferably in the presence of a base such as diisopropylethylamine, sodium carbonate or other acid scavenger such as propylene oxide.

Intermediates of general formula (VI) in which $X^1$ is a group —C=O may be reduced to the corresponding intermediate in which $X^1$ is a group —CH(OH)— using for example a metal hydride such as sodium borohydride in a solvent e.g. ethanol.

Iminoketones of general formula (VI) i.e. in which $X^2$ is a group —CH=N— may be obtained from a phenylglyoxal derivative of formula (X):

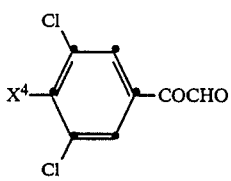

by reaction with an amine of formula (IX) in which Y' represents a hydrogen atom in a solvent such as benzene, tetrahydrofuran or an alcohol e.g. ethanol at temperatures up to the reflux. The phenylglyoxal derivatives of formula (X) may be obtained from a haloketone of formula (VIII) by the action of a dialkylsulphoxide such as dimethylsulphoxide.

Intermediates of general formula (VI) in which $X^3$ is a group —COX— may be prepared by acylation of an amine of formula (XI):

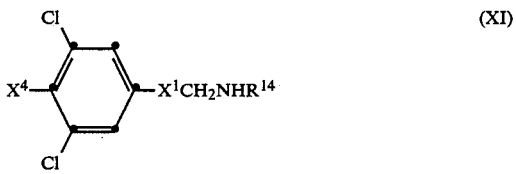

where $R^{14}$ is a hydrogen atom using an ester or an activated derivative of an acid of formula (XII):

$$ArYCH_2OCH_2XCO_2H \quad (XII).$$

Suitable activated derivatives include the acid chloride, an anhydride or imidazolide. The reaction may be optionally carried out in a solvent such as tetrahydrofuran, benzene or chloroform, optionally in the presence of a base such as pyridine or triethylamine. The acids (XII) may be used directly if a coupling agent such as dicyclohexylcarbodiimide is added.

Acids of formula (XII) may be obtained by treatment of an alcohol of general formula (XIII)

$$ArYCH_2OCH_2XCH_2OH \quad (XIII)$$

with a suitable oxidising agent, for example pyridinium dichromate in a solvent such as dimethylformamide.

Intermediates of formula (VI) in which $-X^2-X^3-$ represents $-CH_2N=CR^2X-$ may be obtained by reaction of an amine of formula (XI) in which $R^7$ is a hydrogen atom with a compound of formula (IV) in a solvent such as acetonitrile.

Intermediates of formula (VI) in which $X^2$ is —CONH— may be prepared by reaction of an amine of formula (IX) in which Y' is a hydrogen atom with an acid of formula (XIV):

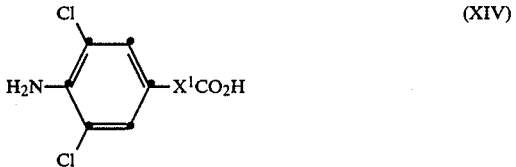

in the presence of a coupling agent such as dicyclohexylcarbodiimide. The acids of formula (XIV) may be prepared by methods analogous to conventional methods for the preparation of α-keto- and α-hydroxy carboxylic acids.

Intermediates of formulae (II), (III), (IV), (VIII), (IX) and (XIII) are either known compounds or may be prepared by methods analogous to those described for the preparation of known compounds.

Suitable methods for preparing intermediates of formulae (III), (IV), (IX) and (XIII) are described in UK Patent Specifications Nos. 2140800A and 2159151A and in the exemplification included hereinafter.

In addition, for the preparation of ketones of formula (IV) (in which $R^2$ represents an alkyl group), a halide $ArYCH_2OCH_2XHal$ (where X represents a bond, $C_{1-5}$ alkylene, $C_{2-5}$ alkenylene or $C_{2-5}$ alkynylene) may be reacted with an appropriate β-ketoester or β-diketone under basic conditions to give an alkylated derivative, which on hydrolysis affords a ketone of formula (IV).

The following examples illustrate the invention. Temperatures are in °C. 'Dried' refers to drying using magnesium sulphate or sodium sulphate except where otherwise stated. Thin layer chromatography (t.l.c.) was carried out over $SiO_2$, and flash column chromatography (FCC) was carried out on silica (Merck 9385) using, unless otherwise stated, one of the following solvent systems: A-toluene:ethanol:0.88 ammonia; B-toluene:ethanol: triethylamine; C-ethyl acetate:hexane:-triethylamine; D-ethylacetate:methanol:triethylamine; E-cyclohexane:ethyl acetate:triethylamine. The following abbreviations are used: THF-tetrahydrofuran; EA-ethyl acetate; ER-diethyl ether; CX-cyclohexane; H-hexane; DMF-dimethylformamide; DCM-dichloromethane; TE-triethylamine; ME-methanol; T-toluene; ET-ethanol; BTPC-bis(triphenylphosphine)palladium (II) chloride; DEA-N,N-diisopropylethylamine.

INTERMEDIATE 1 referred to below is 1-(4-amino-3,5-dichlorophenyl)-2-bromo-1-ethanone.

INTERMEDIATE 2

(a) 1-[2-[(6-Bromohexyl)oxy]ethyl]-4-nitrobenzene

4-Nitrobenzeneethanol (10.25 g), 1,6-dibromohexane (27 ml) tetra-n-butylammonium bisulphate (1.7 g) and 12.5M aqueous sodium hydroxide (55 ml) were stirred together for 40 h. The mixture was diluted with water (250 ml), extracted with ER (3×350 ml) and the combined extracts were washed consecutively with water (250 ml) and brine (250 ml), dried and evaporated to give an oil (42.6 g). The oil was purified by FCC eluting with ER-CX (0:100→1:19) to give the title compound as a yellow oil (9.52 g). T.l.c. (ER-CX 1:19) Rf 0.11. The following compounds were similarly prepared:

(b) 1-[2-[(5-Bromopentyl)oxy]ethyl]-4-methylbenzene (17.9 g) as a colourless oil, from 4-methylbenzeneethanol (10.0 g) and 1,5-dibromopentane (50.7 g) with stirring at room temperature for 72 h. T.l.c. (ER-CX 1:19) Rf 0.29.

(c) 1-[3-[(5-Bromopentyl)oxy]propyl]-3,5-bis(phenylmethoxy)benzene (4.98 g) as a colourless oil, from 3,5-bis(phenylmethoxy)benzenepropanol (5.0 g) and 1,5-dibromopentane (5.9 ml) with stirring at room temperature for 16 h. T.l.c. (ER-CX 1:19) Rf 0.13.

INTERMEDIATE 3

[2-[(5-Bromo-2-pentynyl)oxy]ethyl]benzene (i) [2-[(2-Propynyl)oxy]ethyl]benzene

A mixture of benzenethanol (12.2 g), 3-bromo-1-propyne (12.0 ml), 40% aqueous sodium hydroxide (20 ml) and tetrabutylammonium bisulphate (1 g) was stirred overnight. Water (100 ml) was added and the mixture was extracted with ER (2×100 ml). The organic extracts were washed with water and brine, dried and concentrated to a dark oil which was purified by FCC eluting with CX-ER (19:1) to give the title compound as a pale yellow oil (12.3 g) T.l.c. (CX-ER 19:1) Rf 0.50.

(ii) 5-(2-Phenylethoxy)-3-pentyn-1-ol n-Butyl lithium (1.6M in hexane, 35 ml) was added to a stirred solution of the product of step (i) (8.0 g) in dry THF (50 ml) at −78° under nitrogen. Boron trifluoride etherate (6.8 ml) was added and the mixture was stirred at −78° for 30 min. Oxirane (7 ml) was added and the mixture was stirred at −78° for 1 h, treated with saturated saturated aqueous ammonium chloride (100 ml), allowed to warm to room temperature, and extracted with ER (2×100 ml). The organic extracts were washed with water and brine, dried and concentrated to an orange oil which was purified by FCC eluting with H-ER (2:1) to give the title compound as a pale yellow oil (3.95 g). T.l.c. (H-ER 2:1) Rf 0.10.

(iii) [2-[(5-Bromo-2-pentynyl)oxy]ethyl]benzene

A solution of triphenylphosphine (5.25 g) in dry DCM (15 ml) was added to a solution of the product of step (ii) (3.9 g) and carbon tetrabromide (6.63 g) in dry DCM (25 ml) at 0° over 10 min. The yellow solution was stirred at 0° for 30 min, evaporated onto silica (Merck 9385) and purified by FCC eluting with H→H-ER (3:1) to give the title compound as a colourless oil (2.7 g). T.l.c. (H-ER 2:1) Rf 0.69.

INTERMEDIATE 4

N-[1-Methyl-5-(2-phenylethoxy)pentyl]benzenemethanamine (i) 6-(2-Phenylethoxy)-2-hexanone

[2-(4-Bromobutoxy)ethyl]benzene (10.0 g) in dry ether (80 ml) was added dropwise to magnesium turnings (0.946 g) under nitrogen with stirring to give a gentle reflux. The reaction mixture was refluxed for 1 h, allowed to cool to room temperature and added dropwise to acetic anhydride (8.07 g) in dry ether (55 ml) at −70° under nitrogen with stirring over 1.5 h. The reaction mixture was stirred at −70° for 2 h, allowed to warm to −10°, then treated with saturated ammonium chloride (100 ml). The organic layer was separated and the aqueous layer re-extracted with ER (150 ml). The combined organic extracts were washed with 2N aqueous sodium hydroxide (150 ml), brine (150 ml), dried and evaporated to give an oil (7.54 g) which was purified by FCC eluting with ER-CX (1:3) to give the title compound as a colourless oil (4.34 g). T.l.c. (ER-CX 1:3) Rf 0.25.

(ii) N-[1-Methyl-5-(2-phenylethoxy)pentyl]benzene methanamine

The product of step (i) (4.16 g) and benzylamine (2.03 g) in toluene (50 ml) was refluxed using a Dean-Stark apparatus for 1 h. The toluene solution in ethanol (100 ml) was hydrogenated over pre-reduced 5% platinum oxide on charcoal (0.40 g). The reaction mixture was filtered (hyflo) and evaporated to give an oil (5.73 g) which was purified by FCC eluting with EA-CX (1:4)+1% TE to give the title compound as a yellow oil (4.51 g). T.l.c. (EA-CX 1:4+few drops TE) Rf 0.11.

INTERMEDIATE 5

2,2,2-Trifluoro-N-[6-[2-[4-(4-morpholinyl)phenyl]ethoxy]hexyl]-N-(phenylmethyl)-acetamide A solution of Intermediate 13 (10.0 g), 2-chloroethyl ether (3.38 g), N,N-diisopropylethylamine (6.14 g) and sodium iodide (7.11 g) in DMF (500 ml) was stirred at 100° for 2 days under nitrogen. The solvent was evaporated and water (200 ml) was added to the residue. The mixture was extracted with EA (3×200 ml) and the combined dried (Na2SO4) extracts were concentrated to give an oil (16.5 g) which was purified by FCC eluting with ER-CX (1:2) to give the title compound as an orange oil (3.49 g). T.l.c. (ER-CX 1:1) Rf 0.26.

INTERMEDIATE 6

N-[6-[2-[4-(4-Morpholinyl)phenyl]ethoxy]hexyl]benzenemethanamine

Intermediate 5 (3.25 g) in methanol (40 ml) was stirred under nitrogen for 16 h with potassium carbonate (9.0 g). More potassium carbonate (4.5 g) was added and after 24 h water (50 ml) was added. The mixture was extracted with EA (3×50 ml) and the combined extracts were washed with water (50 ml) and brine (50 ml), dried (Na2SO4) and concentrated to give the title compound as an orange oil (2.59 g). T.l.c. (EA+few drops TE) Rf 0.18.

INTERMEDIATE 7

N-[4-[2-[[6-[(Phenylmethyl)amino]hexyl]oxy]ethyl]phenyl]acetamide

Acetic anhydride (1.53 g) in DCM (25 ml) was added dropwise to an ice-cooled solution of Intermediate 13 (6.34 g) in pyridine (1.19 g) and DCM (25 ml) under nitrogen. After 4 h at room temperature the solvent was evaporated and the residual oil in methanol (40 ml) was stirred under nitrogen with potassium carbonate (9.0 g) for 40 h, more potassium carbonate (4.0 g) being added after 24 h. The mixture was diluted with water (100 ml) and extracted with EA (3×100 ml). The combined extracts were washed with water (100 ml) and brine (100 ml), dried (Na2SO4) and concentrated to an oil (5.19 g) which was purified by FCC eluting with (EA-TE 100:1) to give the title compound as an orange oil (2.94 g). T.l.c. (EA+few drops TE) Rf 0.15.

INTERMEDIATE 8

(a) N-[6-(2-Phenylethoxy)hexyl]benzenemethanamine

[2-[(6-Bromohexyl)oxy]ethyl]benzene (4.0 g) was added dropwise to benzylamine (20 ml) at 110°. The solution was heated at 110°-120° for 90 min, cooled, and treated with hydrochloric acid (2M; 125 ml). The mixture was extracted with EA (2×100 ml) and the extract was washed with aqueous sodium carbonate (100 ml) and brine (100 ml), dried and evaporated. Distillation of the residue gave the title compound as a colourless oil (3.2 g) b.p. 180°-190°/0.1 mmHg. T.l.c. (CX-ER 1:1) Rf 0.25.

(b) N-[5-(2-Phenylethoxy)pentyl]benzenemethanamine (8.6 g) was prepared in a similar manner from [2-[(5-bromopentyl)oxy]ethyl]benzene (10 g) and benzylamine (30 ml). The undistilled product was used without further purification in Example 1(c).

INTERMEDIATE 9

(a) N-[6-[2-(4-Nitrophenyl)ethoxy]hexyl]benzenemethanamine

Intermediate 2(a) (25.9 g) was added dropwise over 40 min to benzylamine (60.76 g) at 120° (bath). After 2 h at 120° the mixture was cooled and water (750 ml) and 2N aqueous hydrochloric acid (375 ml) were added. The mixture was extracted with EA (3×800 ml) and the combined extracts were washed with 2N aqueous sodium carbonate (1 l), brine (500 ml), dried (Na$_2$SO$_4$) and evaporated. The resultant oil (30.4 g) was purified by FCC eluting with EA-CX-TE (25:75:1) to give the title compound as an orange oil (22.58 g). T.l.c. (EA-CX 1:2 with a few drops of TE) Rf 0.33. The following compound was prepared in a similar manner:

(b) N-[5-[3-[3,5-bis(phenylmethoxy)phenyl]propoxy]pentyl]benzenemethanamine, by adding Intermediate 2(c) (2.5 g) to benzylamine (4.3 ml) at 120° under nitrogen with stirring over 5 min, and keeping the reaction mixture at 120° for 4 h before pouring into the hydrochloric acid-water mixture. Final purification by FCC eluting with EA-CX (1:2) with a few drops of TE gave the title compound as a colourless oil (2.44 g). T.l.c. (EA-CX (1:2)+few drops TE) Rf 0.2.

INTERMEDIATE 10

(a) N-[5-[3-(4-Methoxyphenyl)propoxy]pentyl]benzenemethanamine hydrochloride

1-[3-[(5-Bromopentyl)oxy]propyl]-4-methoxybenzene (2.0 g) was added to benzylamine (6 ml) at 120° under nitrogen. The solution was stirred for 2 h at 120° then added (hot) to 2N hydrochloric acid (50 ml) and water (25 ml). The resulting precipitate was collected by filtration, washed with 2N hydrochloric acid, water and ER then dried at 50° under vacuum to give the title compound as a white solid (1.79 g) m.p. 118°–121°. The following compound was prepared in a similar manner:

(b) N-[5-[2-(4-Methylphenyl)ethoxy]pentyl]benzenemethanamine hydrochloride (8.41 g) as a white solid, m.p. 138°, from Intermediate 2(b) and benzylamine (20 ml).

INTERMEDIATE 11

N-[5-(2-(4-Fluorophenyl)ethoxy]pentyl]benzenemethanamine hydrochloride

1-[2-[(5-Bromopentyl)oxy]ethyl]-4-fluorobenzene (7.95 g) was added dropwise over 10 min to benzylamine (24 ml) at 125° under nitrogen. The reaction mixture was stirred for 3.5 h at 120° and the hot reaction mixture was poured into 2N aqueous hydrochloric acid (170 ml) and water (220 ml). After stirring for 15 min the precipitate was collected by filtration to give the title compound as a white solid (7.41 g) m.p. 112°.

INTERMEDIATE 12

1,1-Dimethyl-5-[2-[4-(4-morpholinyl)phenyl]ethoxy]pentanamine (i) 4-(4-Morpholinyl)benzeneethanol 4-Aminobenzeneethanol (20.2 g), 2-chloroethyl ether (21.1 g), N,N-diisopropylethylamine (38.1 g) and potassium iodide (48.8 g) in DMF were heated to 80° under nitrogen for 60 h. The solvent was evaporated and the residue (~143 g) was purified by FCC eluting with ER-CX (1:1→1:0) to give the title compound as a pink-white solid (17.7 g) m.p. 57°.

(ii) 4-[4-[2-[(4-Bromobutyl)oxy]ethyl]phenyl]morpholine

The product of stage (i) (17.6 g), 1,4-dibromobutane (30 ml), 12.5M aqueous sodium hydroxide (100 ml) and tetra-n-butylammonium bisulphate (2.0 g) were stirred rapidly at room temperature for 16 h. The mixture was diluted with water (400 ml), extracted with ER (3×400 ml) and the combined extracts were washed consecutively with water (400 ml) and brine (400 ml), dried and concentrated to give an oil (53.5 g) which was purified by FCC eluting with ER-CX (0.1→1:5) to give the title compound as an orange oil (20.1 g). T.l.c. ER-hexane (1:5) Rf 0.1.

(iii) 2,2-Dimethyl-6-[2-[4-(4-morpholinyl)phenyl]ethoxy]hexanoic acid n-Butyllithium in hexane (1.53M, 113.5 ml) was added dropwise to N,N-diisopropylamine (17.9 g) in THF (100 ml) at −78° under nitrogen. The mixture was warmed to 0°, stirred for 1 h and treated dropwise with isobutyric acid (7.65 g) in THF (20 ml). The resulting suspension was stirred at room temperature for 3 h, and the product of stage (ii) (20.0 g) was added dropwise. The reaction mixture was stirred for 16 h at room temperature and the solvent was evaporated. The resultant oil was partitioned between EA (250 ml) and water (250 ml). The aqueous layer was acidified to pH6 with 2N aqueous hydrochloric acid and the organic extract was separated. The aqueous layer was extracted with EA (250 ml) and the combined extracts were concentrated to leave the title compound as an orange oil (20.4 g). T.l.c. (ER) Rf 0.53.

(iv) (Phenylmethyl) [5-[2-[4-(4-morpholinyl)phenyl]ethoxy]pentyl]carbamate

Ethyl chloroformate (3.29 g) in acetone (10 ml) was added dropwise to a solution of the product of stage (iii) (10.0 g) and triethylamine (3.0 g, 30 mmol) in acetone (100 ml) and water (10 ml) at 0°. The mixture was stirred at 0° for 40 min and sodium azide (2.0 g) in water (25 ml) was added dropwise. The resulting suspension was stirred at room temperature for 45 min, diluted with water (200 ml) and extracted with T (2×200 ml). The dried (Na$_2$SO$_4$) extract was heated at 75°–80° for 2.5 h and evaporated. The residue was treated with benzyl alcohol (20 ml), heated at 75°–80° for 60 h and benzyl alcohol was removed by distillation (~1 mmHg). The resulting oil was purified on a column of silica (Merck 9385) eluted with ER-CX (1:2) to give the title compound, as a yellow oil (4.74 g). T.l.c. ER-CX (1:2) Rf 0.13.

(v) 1,1-Dimethyl-5-[2-[4-(4-morpholinyl)phenyl]ethoxy]pentanamine

The product of stage (iv) (7.50 g) in ethanol (80 ml) was hydrogenated over 10% palladium on charcoal (50% paste in water, 1.0 g). The reaction mixture was filtered (hyflo) and the solvent was evaporated to give an oil (5.99 g) which was purified by FCC eluting with EA-ME-TE (66:33:1) to give the title compound as a yellow oil (2.84 g). T.l.c. EA-ME-TE (66:33:1) Rf 0.26.

INTERMEDIATE 13

N-[6-[2-(4-Aminophenyl)ethoxy]hexyl]-2,2,2-trifluoro-N-(phenylmethyl)acetamide (i) 2,2,2-Trifluoro-N-[6-[2-(4-nitrophenyl)ethoxy]hexyl]-N-(phenylmethyl)acetamide Intermediate 2(a) (5.2 g) was added dropwise over 30 min to benzylamine (12.25 g) at 120° (bath). The mixture was maintained at 120° for 2 h, cooled and water (150 ml) and 2N aqueous hydrochloric acid (75 ml) were added. The mixture was extracted with EA (2×200 ml, 1×100 ml) and the combined extracts were washed with 2N aqueous sodium carbonate (200 ml), brine (200 ml), dried (Na₂SO₄) and evaporated to give an oil (5.76 g). The oil in DCM (15 ml) and TE (2.5 ml) was ice-cooled and treated with trifluoroacetic anhydride (2.55 ml) in DCM (10 ml) over 5 min. The reaction mixture was stirred for a further 1 h at room temperature. After 64 h DCM (20 ml) was added and the mixture was washed with 2N aqueous hydrochloric acid (20 ml), 8% aqueous sodium bicarbonate (20 ml), water (20 ml), brine (20 ml), dried (Na₂SO₄) and evaporated to give an oil (7.46 g) which was purified by FCC eluting with EA-CX-TE (20:80:1) to give the title compound as a yellow oil (5.91 g). T.l.c. (EA-CX (1:2)+few drops TE) Rf 0.45.

(ii) N-[6-[2-(4-Aminophenyl)ethoxy]hexyl]-2,2,2-trifluoro-N-(phenylmethyl)acetamide A solution of the product of step (i) (4.95 g) in ethanol (100 ml) was hydrogenated at ambient temperature and pressure over pre-reduced 5% platinum on charcoal (0.5 g). The reaction mixture was filtered (hyflo) and evaporated to give an oil (3.79 g), which was purified by FCC eluting with EA-CX (1:2) with 1% TE to give the title compound as a yellow oil (3.57 g). T.l.c. (EA-CX (1:2)+few drops TE) Rf 0.24.

INTERMEDIATE 14

N-[5-[2-[4-Methoxyphenyl]ethoxy]pentyl]benzenemethanamine hydrochloride (i) 1-[2-[(5-Bromopentyl)oxy]ethyl]-4-methoxybenzene A mixture of 4-methoxybenzeneethanol (7.0 g), 1,5-dibromopentane (20 ml), 50% aqueous sodium hydroxide (30 ml) and tetrabutylammonium bisulphate (1 g) was stirred at room temperature overnight, water (100 ml) was added and the mixture was extracted with ER (2×100 ml). The organic extracts were washed with water and brine, dried and concentrated in vacuo to give an oil which was purified by FCC eluting with hexane→hexane-ER (9:1) to give the title compound as a colourless liquid (10.5 g). T.l.c. hexane-ER (9:1) Rf 0.28.

(ii) N-[5-[2-[4-Methoxyphenyl]ethoxy]pentyl]benzenemethanamine hydrochloride

The product of stage (i) (5 g) was added to benzylamine (15 ml) at 140° under nitrogen. After 2 h the reaction mixture was poured into 2N hydrochloric (150 ml) and water (150 ml). The precipitate was collected by filtration, washed with water and ER then dried under vacuum at 50° to give the title compound as a white solid (3.4 g) m.p. 123°-126°.

INTERMEDIATE 15

1-Bromo-6-[(2-propynyl)oxy]hexane, (15.0 g) from propargyl alcohol (5.6 g) and 1,6-dibromohexane (73.2 g) in a similar manner to Intermediate 2a. Purification by FCC eluting with CX followed by CX-ER (19:1). T.l.c. (CX-ER 9:1) Rf 0.4.

INTERMEDIATE 16

N-[6-[(2-Propynyl)oxy]hexyl]benzenemethanamine

Intermediate 15 (1.5 g) was added dropwise to benzylamine (10 ml) at 120°. The solution was stirred at ca 120° for 1 h, cooled, and added to hydrochloric acid (2M; 50 ml). The mixture was basified with aqueous sodium hydroxide (2M) and extracted with ER (2×200 ml). The dried extract was evaporated and excess benzylamine was removed under reduced pressure (ca 10 ml). The residue was purified by FCC eluting with ER to give the title compound (0.96 g). T.l.c. (ER) Rf 0.1.

INTERMEDIATE 17

Ethyl 4-[3-[[6-[(phenylmethyl)amino]hexyl]oxy]1-butynyl]-benzoate

Ethyl 4-iodobenzoate (4.65 g), Intermediate 16 (4.12 g), bis(triphenylphosphino)palladium(II)chloride (120 mg) and copper (I) iodide (70 mg) in diethylamine (90 ml) were stirred under nitrogen at room temperature for 16 h. ER (100 ml) was added and the precipitate was collected by filtration. The filtrate was concentrated and the resultant oil was purified by FCC eluting with ER-TE (100:1) to give the title compound as an orange oil (5.96). T.l.c. (ER-TE 100:1). Rf 0.16.

INTERMEDIATE 18

Ethyl 4-[3-[[6-[[(4-amino-3,5-dichlorophenyl) 2-hydroxyethyl](phenylmethyl)amino]hexyl]oxy]1-propynyl]benzoate 1-(4-Amino-3,5-dichlorophenyl)-2-bromoethanone (3.08 g), Intermediate 17 (4.29 g), and N,N-diisopropylethylamine (1.41 g) in THF (50 ml) was left to stand for 16 h under nitrogen at room temperature. The precipitate was collected by filtration and the filtrate was concentrated. The resulting oil in ME (60 ml) was ice-cooled and treated portionwise with sodium borohydride (1.55 g), stirred under nitrogen for 24 h and water (200 ml) was added. The mixture was extracted with EA (3×150 ml) and, the combined extracts were washed with water (200 ml) and brine (200 ml), dried (Na₂SO₄) and concentrated to give an oil (6.48 g) which was purified by FCC eluting with T to give impure title compound as a red oil (5.06 g). T.l.c. T Rf 0.2.

INTERMEDIATE 19

(Z)-N-[4-[3-[[6-[(Phenylmethyl)amino]hexyl]oxy]-1-propenyl]phenyl]-methanesulphonamide, hydrochloride (Z)-N-[4-[3-[(6-Bromohexyl)oxy]-1-propenyl]-phenyl]methanesulphonamide (2.0 g) was added to benzylamine (6 ml) at 125°, under nitrogen. The reaction mixture was stirred at 125° for 3 h, cooled to room temperature and added to 2N hydrochloric acid (50 ml) and water (20 ml). The resultant white solid was collected by filtration, washed in turn with 2N hydrochloric acid, water and ether then dried in vacuo at 50° to give the title compound as a white powder (1.0 g) m.p. 133°-134°.

INTERMEDIATE 20

(Z)-N-[4-[3-[[6-[[2-(4-Amino-3,5-dichlorophenyl)-2-hydroxyethyl]-(phenylmethyl)amino]hexyl]oxy]-1-propenyl]phenyl]methane sulphonamide A suspension of Intermediate 1 (520 mg), Intermediate 19 (850 mg) and DEA (500 mg) in THF (25 ml) was stirred at room temperature overnight. After filtration, the filtrate was concentrated to an oil which was dissolved in methanol (20 ml) cooled in an ice-bath and treated with sodium borohydride (250 mg). The pale yellow solution was stirred at room temperature overnight, the methanol was evaporated and the residue partitioned between water (25 ml) and ethyl acetate (25 ml). The organic phase was washed with water and brine, dried and concentrated to a red oil which was purified by FCC eluting with System E (75:25:1) to give the title compound as a colourless oil (540 mg). T.l.c. (System E 75:25:1) Rf 0.09.

INTERMEDIATE 21

4-Iodo-N,N-dimethylbenzeneethanamine, hydrochloride

4-Bromo-N,N-dimethylbenzeneethanamine, hydrochloride (0.65 g) was partitioned between ethyl acetate (10 ml) and 8% sodium bicarbonate (10 ml). The aqueous layer was extracted with ethyl acetate (10 ml), and the combined organic extracts were dried and concentrated to give the free base (0.57 g). n-Butyl lithium (1.6M in hexane, 1.72 ml) was added to a solution of the free base (0.57 g) in THF (10 ml) at −78°, and the mixture was stirred under nitrogen for 30 min. A solution of iodine (0.63 g) in THF (10 ml) was added dropwise and after 10 min the reaction was quenched by addition of saturated ammonium chloride (10 ml). The THF was evaporated and the aqueous residue was extracted with ethyl acetate (2×15 ml). The organic extracts were washed with 10% sodium thiosulphate (15 ml) and brine (15 ml), dried and concentrated to yield a brown oil. The oil in ether (10 ml) and dichloromethane (2 ml) was treated with ethereal hydrogen chloride and the resultant precipitate was collected by filtration and dried to give the title compound as a white solid (0.54 g).

Analysis Found: C,38.77; H,4.87; N,4.39; Cl,11.36; I,40.67. $C_{10}H_{14}IN.HCl$ requires C,38.55; H,4.85; N,4.5; Cl,11.38; I,40.73%.

INTERMEDIATE 22

N-(4-Iodophenyl)-N-methylmethanesulphonamide

A mixture of N-(4-iodophenyl)methanesulphonamide (4.3 g), 50% aqueous sodium hydroxide (25 ml), iodomethane (5 ml), dichloromethane (10 ml) and tetrabutylammonium bisulphate (0.5 g) was stirred vigorously for 2 h. Water (50 ml) was added and the mixture was extracted with ether (3×50 ml). The organic extracts were washed with water and brine, dried and concentrated to a solid which was triturated with hexane to give the title compound as white crystals (4.1 g) m.p. 106°–107°.

INTERMEDIATE 23

2-(4-Iodophenoxy)-N,N-dimethylacetamide

Dimethylamine (33% w/w in IMS, 5.85 ml) was added dropwise to a suspension of (4-iodophenoxy)acetyl chloride (9.49 g) in triethylamine (50 ml) at 0° under nitrogen. The suspension was stirred for 2 h at 0° and partitioned between ethyl acetate (300 ml) and 8% aqueous sodium bicarbonate (300 ml). The organic layer was dried and the solvent was evaporated to leave an oil which was purified by FCC eluting with diethyl ether to give the title compound as a white solid (3.96 g), m.p. 63°–65°.

INTERMEDIATE 24

4-Iodo-N,N-dimethylbenzeneacetamide

4-Iodophenylacetyl chloride (5.15 g) was added portionwise to dimethylamine (0.90 g) in triethylamine (25 ml) at 0°. The suspension was stirred at 0° for 2 h and chloroform (100 ml) was added. The organic phase was washed with 8% aqueous sodium bicarbonate (50 ml), dried and concentrated to give a red solid (5.0 g) which was purified by FCC eluting with ether followed by ethyl acetate to give the title compound as a yellow solid (2.58 g) m.p. 75°–77°.

INTERMEDIATE 25

N,N-Dimethyl-4-[4-[5-[(phenylmethyl)amino]pentyloxy]butyl] benzene-acetamide

Intermediate 33 (1.60 g) was added dropwise to benzylamine (3.5 ml) at 120° under nitrogen. The solution was stirred for 3 h at 120° and poured into 0.8N aqueous hydrochloric acid (65 ml). The aqueous mixture was extracted with ethyl acetate (3×30 ml) and the combined extracts were washed with 8% aqueous sodium bicarbonate (50 ml) and brine (50 ml), dried and concentrated to give an oil (0.56 g). The combined aqueous phases were re-extracted with ethyl acetate (2×50 ml), dried and concentrated to give an oil (0.92 g). The two oils were combined and purified by FCC eluting with ethyl acetate-triethylamine (100:1) to give the title compound as a pale yellow oil (1.00 g), t.l.c. (Ethyl acetate-triethylamine 100:1) Rf 0.1.

INTERMEDIATE 26

N-[[3-[3-[[6-[(Phenylmethyl)amino]hexyl]oxy]-1-propynyl]phenyl]-methyl]acetamide A suspension of N-[(3-iodophenyl)methyl]acetamide (3.91 g), N-[6-[(2-propynyl)oxy]hexyl]benzenemethanamine (3.48 g), BTPC (100 mg) and copper iodide (60 mg) in diethylamine (75 ml) was stirred at room temperature under nitrogen for 20 h. The reaction mixture was poured into diethyl ether (100 ml) and filtered. The filtrate was concentrated to give an oil (6.62 g) which was purified by FCC eluting with System D (100:0:1→100:10:1) to give the title compound as a red oil (4.60 g), t.l.c. (Ethyl acetate-triethylamine 100:1) Rf 0.12.

Intermediates 27–30 were prepared in a similar manner:

INTERMEDIATE 27

N,N-Dimethyl-4-[3-[[6-[(phenylmethyl)amino]hexyl]oxy]-1-propynyl]benzamide

From 4-iodo-N,N-dimethylbenzamide (2.5 g) and N-[6-[(2-propynyl)oxy]- hexyl]benzenemethanamine (2.23 g). FCC purification eluting with ethyl acetate-triethylamine (100:1) gave the title compound as an orange oil (2.96 g), t.l.c. (Ethyl acetate+few drops triethylamine) Rf 0.15.

INTERMEDIATE 28

N,N-Dimethyl-2-[4-[3-[[6-[(phenylmethyl)amino]hexyl]oxy]-1-propynyl]-phenoxy]acetamide From Intermediate 23 (3.91 g) and N-[6-[(2-propynyl)oxy]hexyl]- benzenemethanamine (3.14 g). FCC purification eluting with System C (83:17:1) gave a product (3.87 g) which was re-columned as previously but using ethyl acetate-triethylamine (100:1) as the eluant to give the title compound as an orange oil (1.44 g), t.l.c. (Ethyl acetate+few drops triethylamine) Rf 0.3.

INTERMEDIATE 29

N-Methyl-N-[4-[3-[[6-[(phenylmethyl)amino]hexyl]oxy]-1-propynyl]-phenyl]methanesulphonamide From Intermediate 22 (1.8 g) and N-[6-[(2-propynyl)oxy]hexyl]-benzenemethanamine (1.5 g), except that triethylamine/THF (1:1, 50 ml)) was used instead of diethylamine. FCC purification eluting with System B (95:5:1) gave the title compound as an orange oil (2.0 g), t.l.c. (System B 95:5:1) Rf 0.13.

INTERMEDIATE 30

4-[3-[[6-[[2-(4-Amino-3,5-dichlorophenyl)-2-hydroxyethyl](phenylmethyl)amino]hexyl]oxy]-1-propynyl) benzamide From Intermediate 41 (550 mg) and 4-iodobenzamide (250 mg), except that diethylamine/THF (4:1, 10 ml) was used instead of diethylamine, and addition of the reaction mixture to ether followed by filtration was omitted. FCC purification of the concentrated reaction mixture eluting with System B (90:10:1) gave the title compound as a pale yellow oil (540 mg), t.l.c. System B 90:10:1) Rf 0.35.

INTERMEDIATE 31

N-[4;[3-[[6-[[2-(4-Amino-3,5-dichlorophenyl)-2-hydroxyethyl](phenylmethyl)amino]hexyl]oxy]-1-propynyl]-phenyl]-2-(dimethylamino) acetamide A suspension of Intermediate 41 (1.0 g), 2-(dimethylamino)-N-(4- iodophenyl)acetamide (680 mg), dicyclohexylamine (450 mg), BTPC (50 mg) and copper (I) iodide (10 mg) in acetonitrile (15 ml) was stirred under nitrogven for 3 hr. Ether (25 ml) was added, the precipitate was removed by filtration, the solvent was evaporated and the residue purified by FCC eluting with System C (50:50:1) to give the title compound as a yellow oil (800 mg), t.l.c. (System A 80:20:2) Rf 0.53.

INTERMEDIATE 32

4-[4-[3-[[6-[(Phenylmethyl)amino]hexyl]oxy]-1-propynyl]benzoyl]-morpholine 4-(4-Iodobenzoyl)morpholine (4.0 g) and N-[6-[(2-propynyl)oxy]- hexyl]benzenemethanamine (3.09 g) were reacted according to the method of Intermediate 31. FCC purification eluting with ethyl acetate-triethylamine (100:1) gave the title compound as a yellow oil (2.21 g), t.l.c. (Ethyl acetate-triethylamine 100:1) Rf 0.2.

INTERMEDIATE 33

4-[4-[(5-Bromopentyl)oxy]butyl]-N,N-dimethylbenzeneacetamide

A mixture of Intermediate 24 (2.50 g), 1-bromo-5-(3-butynyloxy)pentane (1.90 g), dicyclohexylamine (1.73 g), BTPC (50 mg) and copper iodide (10 mg) was stirred in acetonitrile (30 ml) under nitrogen for 2 h. Ether (80 ml) was added, the mixture was filtered, the filtrate was concentrated and the residue was refluxed in ethanol (100 ml) with charcoal and filtered (hyflo). The solution was hydrogenated over 10% palladium on charcoal (50% paste in water; 1.0 g) for 48 h, filtered (hyflo) and concentrated to give a residue which was purified by FCC eluting with ether-ethyl acetate (100:0→80:20) to give the title compound as a yellow oil (1.62 g), t.l.c. (Ether) Rf 0.12.

INTERMEDIATE 34

(Z)-N-[[3-[3-[[6-[[2-(4-Amino-3,5-dichlorophenyl)-2-hydroxyethyl]-(phenylmethyl)amino]hexyl]oxy]-1-propenyl]phenyl]methyl]acetamide A solution of Intermediate 1 (1.44 g), Intermediate 26 (2.0 g) and DEA (660 mg) in THF (20 ml) was left to stand for 20 h at room temperature under nitrogen. The precipitate was removed by filtration and the filtrate was concentrated to give an oil which was dissolved in methanol (20 ml) cooled in an ice-bath, and treated portionwise with sodium borohydride (750 mg). The reaction mixture was stirred at room temperature under nitrogen for 2 h and concentrated to give an oil to which water (100 ml) was added. The mixture was extracted with ethyl acetate (3×50 ml) and the combined extracts were washed with water (50 ml) and brine (50 ml), dried and concentrated to give an oil which was purified by FCC eluting with System B (95:5:1) to give the title compound as a yellow oil (1.51 g), t.l.c. (System B 95:5:1) Rf 0.13.

Intermediates 35–41 were prepared in a similar manner:

INTERMEDIATE 35

4-[4-[5-[[2-(4-Amino-3,5-dichlorophenyl)-2-hydroxyethyl](phenylmethyl)amino]pentyloxy]butyl]-N,N-dimethylbenzeneacetamide From Intermediate 1 (690 mg) and Intermediate 25 (1.01 g). The sodium borohydride/methanol reaction was continued for 24 h. FCC purification eluting with System C (50:50:1) gave the title compound as a yellow oil (1.12 g), t.l.c. (Ethyl acetate-hexane (1:1)+few drops triethylamine) Rf 0.1.

INTERMEDIATE 36

(Z)-2-[4-[3-[[6-[[2-(4-Amino-3,5-dichlorophenyl)-2-hydroxyethyl]-(phenylmethyl)amino]hexyl]oxy]-1-propenyl]phenoxy]-N,N-dimethyl-acetamide From Intermediate 1 (951 mg) and Intermediate 28 (1.42 g). FCC purification eluting with System B (97:3:1) gave the title compound as a yellow oil (1.11 g), t.l.c. (System B 95:5:1) Rf 0.31.

INTERMEDIATE 37

N-[4-[2-[[6-[[2-(4-Amino-3,5-dichlorophenyl)-2-hydroxyethyl](phenylmethyl)amino]hexyl]oxy]ethyl]phenyl]-methanesulphonamide From Intermediate 1 (0.7 g) and N-[4-[2-[[6-[(phenylmethyl)amino]hexyl]oxy]ethyl]phenyl]methanesulphonamide (1 g). FCC purification eluting with System B (98:2:1) gave the title compound as a yellow oil (1.2 g), t.l.c. (System A 80:20:1) Rf 0.47.

INTERMEDIATE 38

N-[4-[3-[[6-[[2-(4-Amino-3,5-dichlorophenyl)-2-hydroxyethyl](phenylmethyl)amino]hexyl]oxy]-1-propynyl]-phenyl]-N-methylmethanesulphonamide From Intermediate 1 (660 mg) and Intermediate 29 (1.0 g). The sodium borohydride/methanol reaction was continued for 18 h. FCC purification eluting with System C (33:66:1→50:50:1) gave the title compound as a pale yellow oil (320 mg), t.l.c. (hexane-ether-triethylamine 50:50:1) Rf 0.04.

INTERMEDIATE 39

(Z)-4-[3-[[6-[[2-(4-Amino-3,5-dichlorophenyl)-2-hydroxyethyl](phenylmethyl)amino]hexyl]oxy]-1-propenyl]-N,N-dimethylbenzamide From Intermediate 1 (1.0 g) and Intermediate 27 (1.39 g). FCC purification eluting with System B (97:3:1) gave the title compound as a yellow oil (0.93 g), t.l.c. (System B 95:5:1) Rf 0.3.

INTERMEDIATE 40

4-[4-[3-[[6-[[2-(4-Amino-3,5-dichlorophenyl)-2-hydroxyethyl](phenylmethyl)amino]hexyl]oxy]-1-propynyl]benzoyl]morpholine From Intermediate 1 (1.0 g) and Intermediate 32 (1.53 g). The sodium borohydride/methanol reaction was continued for 60 h. FCC purification eluting with System B (97:3:1) gave the title compound as an orange oil (1.54 g), t.l.c. (System B 95:5:1) Rf 0.25.

INTERMEDIATE 41

4-Amino-3,5-dichloro-α-[[(phenylmethyl)[6-[(2-propynyl)oxy]hexyl]amino]methyl]benzenemethanol From Intermediate 1 (1.0 g) and N-[6-[(2-propynyl)oxy]hexyl]benzene- methanamine (870 mg), carrying out the first stage of the reaction for only 25 min. FCC purification eluting with System C (20:80:1) gave the title compound as a colourless oil (1.27 g), t.l.c. (System C 20:80:1) Rf 0.33.

INTERMEDIATE 42

N,N-Bis[2-phenylmethoxy)ethyl]-4-iodobenzeneamine

A mixture of 2,2'-(4-iodophenylimino)bis-ethanol (2 g), benzyl bromide (2.3 g), tetra-n-butylammonium bisulphate (0.4 g) and 50% sodium hydroxide (20 ml) was stirred vigorously for 5 h. The mixture was diluted with water (20 ml), extracted with ethyl acetate (2×20 ml) and the combined extracts were washed consecutively with water (50 ml) and brine (50 ml), dried and evaporated. Purification by FCC eluting with hexane-ether (19:1→9:1) gave the title compound as a pale yellow oil (2.1 g), t.l.c. (hexane-ether 1:1) Rf 0.7.

INTERMEDIATE 43

4-Amino-3,5-dichloro-α-[[[6-[[3-[4-bis[2-(phenylmethoxy)ethyl]amino]phenyl]-2-propynyl]oxy]hexyl](phenylmethyl)amino]methyl]benzenemethanol A solution of Intermediate 41 (1.9 g), Intermediate 42 (1.75 g), BTPC (90 mg) and copper (I) iodide (9 mg) in diethylamine/tetrahydrofuran (4:1, 30 ml) was stirred at room temperature under nitrogen for 2 days. The solvent was evaporated and the residue was purified by FCC eluting with System C (20:80:1→30:70:1) to give the title compound as an orange oil (1.75 g), t.l.c. (System C 20:80:1) Rf 0.17.

INTERMEDIATE 44

4-Amino-3,5-dichloro-α-[[6-[[3-[4-[2-(dimethylamino)ethoxy]phenyl]2-propynyl)oxy]hexyl](phenylmethyl)amino]methyl]benzenemethanol A solution of 2-(4-iodophenoxy)-N,N-dimethylethanamine' (1.57 g), Intermediate 41 (2.94 g), BTPC (100 mg) and copper iodide (10 mg) in diethylamine (30 ml) and acetonitrile (10 ml) was stirred at room temperature under nitrogen for 16 h. The solvent was evaporated and the residue was purified by FCC eluting with System B (95:5:1) to give the title compound as a red oil (3.57 g), t.l.c. (System B 95:5:1) Rf 0.26.

EXAMPLE 1

(a) 4-Amino-3,5-dichloro-α-[[[6-[2-(4-nitrophenyl)ethoxy]hexyl](phenylmethyl)amino]methyl]benzenemethanol Intermediate 1 (794 mg), Intermediate 9(a) (1.0 g) and N,N-diisopropylethylamine (400 mg) in THF (15 ml) were left at room temperature overnight. The mixture was filtered and the filtrate concentrated in vacuo to an oil which was dissolved in methanol (10 ml), cooled in an ice-bath, treated with sodium borohydride (200 mg) and stirred overnight at room temperature. Water (25 ml) was added and the mixture was extracted with EA (3×20 ml). The organic extracts were washed with brine, dried (Na$_2$SO$_4$) and concentrated to an oil which was purified by FCC eluting with CX-EA-TE (80:20:1) to give the title compound as an orange oil (1.3 g). T.l.c. (CX-EA-TE 80:20:1) Rf 0.21. The following compounds were prepared in a similar manner:

(b) 4-Amino-3,5-dichloro-α-[[[6-(2-phenylethoxy)hexyl](phenylmethyl)amino]methyl]benzenemethanol (630 mg) as a colourless oil (t.l.c. (CX-EA-TE 80:20:1) Rf 0.23), from Intermediate 1 (500 mg) and Intermediate 8(a) (607 mg), except that the reaction mixture was decanted from the precipitated needles, which were further washed with ether, before concentrating to an oil, and the reaction with sodium borohydride (100 mg) was carried out for only 1 h.

(c) 4-Amino-3,5-dichloro-α-[[[5-(2-phenylethoxy)pentyl](phenylmethyl)amino]methyl]benzenemethanol (690 mg) as a colourless oil (t.l.c. (CX-EA-TE 66:33:1) Rf 0.25) from Intermediate 1 (500 mg) and Intermediate 8(b) (550 mg), allowing the reaction mixture to stand at room temperature for 5 h, then adding ER (25 ml) before filtering, and evaporating the filtrate. Purification by FCC using CX-EA-TE (66:33:1) as eluent.

(d) 4-Amino-3,5-dichloro-α-[[[6-(4-phenylbutoxy)hexyl](phenylmethyl)amino]methyl]benzenemethanol (1.37 g) as a yellow oil (t.l.c. (EA-CX (1:4)+few drops TE) Rf 0.3) from Intermediate 1 (1.00 g), N-[6-(4-phenylbutoxy)hexyl]benzenemethanamine (1.32 g) and N,N-diisopropylethylamine (0.68 ml) in THF (25 ml) leaving the reaction mixture for 72 h at room temperature under nitrogen, before filtering, and evaporating the filtrate. The resultant residue was dissolved in methanol (20 ml) and treated with sodium borohydride (0.267 g), stirred under nitrogen at room temperature for 3 h and more sodium borohydride (0.108 g) was added. After 1 h the reaction was worked up by the method of Example 1(a).

(e) 4-Amino-3,5-dichloro-α-[[[1-methyl-5-(2-phenylethoxy)pentyl](phenylmethyl)amino]methyl]benzenemethanol (970 mg) as a colourless oil (t.l.c. CX-EA-TE (80:20:1) Rf 0.58), from Intermediate 1 (3.1 g) and Intermediate 4 (3.4 g). Purification by FCC eluting with CX-EA-TE (90:10:1).

(f) 4-Amino-3,5-dichloro-α-[[[5-[2-(4-Fluorophenyl)ethoxy]pentyl](phenylmethyl)amino]methyl]benzenemethanol (0.804 g) as a colourless oil (t.l.c. (EA-CX-TE 20:80:1) Rf 0.27, from Intermediate 1 (1.00 g), Intermediate 11 (1.11 g) and N,N-diisopropylethylamine (0.912 g), except that the reaction mixture was stirred under nitrogen at room temperature for 16 h, and the reaction with sodium borohydride was allowed to proceed for only 3 h.

(g) 4-Amino-3,5-dichloro-α-[[[6-[2-[4-(4-morpholinyl)phenyl]ethoxy]hexyl](phenylmethyl)amino]methyl]benzenemethanol (1.75 g) as a viscous oil (t.l.c. H-EA (4:1) Rf 0.11) from Intermediate 1 (1.0 g) and Intermediate 6 (1.5 g). For treatment with sodium borohydride, the residue was dissolved in ME (40 ml) and THF (10 ml) and, following the reaction, the mixture was concentrated to an oil which was partitioned between EA (50 ml) and water (50 ml). Final purification by FCC eluting with H-EA (9:1→4:1).

(h) N-[4-[2-[[6-[[2-(4-Amino-3,5-dichlorophenyl)-2-hydroxyethyl](phenylmethyl)amino]hexyl]oxy]ethyl]phenyl]acetamide (1.13 g) as a yellow oil (t.l.c. EA-CX (1:1)+few drops TE Rf 0.2), from Intermediate 1 (1.00 g) and Intermediate 7 (1.30 g). The sodium borohydride-methanol reaction mixture was stirred under nitrogen for 24 h. Final purification by FCC eluting with EA-CX-TE (50:50:1).

(i) 4-Amino 3,5-dichloro-α-[[[5-[2-(4-methylphenyl)ethoxy]pentyl](phenylmethyl)amino]methyl]benzenemethanol (0.95 g) as a colourless oil (t.l.c. EA-CX-TE (20:80:1) Rf 0.37), from Intermediate 1 (1.00 g), Intermediate 10(b) (1.23 g) and N,N-diisopropylethylamine (0.912 g). The sodium borohydride-methanol reaction mixture was stirred under nitrogen for 48 h. Final purification by FCC eluting with EA-CX (1:6) with 1% TE.

(j) 4-Amino-α-[[[5-[3-[3,5-bis(phenylmethoxy)phenyl]propoxy]pentyl](phenylmethyl)amino]methyl]-3,5-dichlorobenzenemethanol (2.28 g) as a yellow oil (t.l.c. EA-CX (1:4)+few drops TE Rf 0.23) from Intermediate 1 (1.0 g) and Intermediate 9(b) (1.85 g). The sodium borohydride-methanol reaction was allowed to proceed for 24 h.

(k) 4-Amino-3,5-dichloro-α-[[[5-[3-(4-methoxyphenyl)propoxy]pentyl](phenylmethyl)amino]methyl]benzenemethanol (510 mg) as a colourless oil (t.l.c. CX-EA (9:1) Rf 0.36) from Intermediate 1 (600 mg), Intermediate 10(a) (950 mg) and N,N-diisopropylethylamine (650 mg). After the sodium borohydride-methanol reaction the mixture was concentrated to an oil and partitioned between water (50 ml) and EA (50 ml). Final purification by FCC eluting with CX-EA (9:1).

(l) 4-Amino-3,5-dichloro-α-[[[5-[2-(4-methoxyphenyl)ethoxy]pentyl](phenylmethyl)amino]methyl]benzenemethanol (240 mg) as a colourless oil (t.l.c. hexane-EA-TE 80:20:1) Rf 0.28, from Intermediate 1 (325 mg), Intermediate 14 (430 mg) and N,N-diisopropylethylamine (300 mg), except that the reaction with sodium borohydride was carried out for only 6 h, after which the solvent was evaporated and the residue was partitioned between 8% aqueous sodium bicarbonate (25 ml) and ethyl acetate (25 ml). Purification by FCC using hexane-EA-TE (90:10:1) as eluent. T.l.c. silica (hexane-EA-TE 80:20:1) Rf 0.28.

EXAMPLE 2

(a) 4-Amino-3,5-dichloro-α-[[[6-(2-phenylethoxy)hexyl]amino]methyl]benzenemethanol Example 1(b) (300 mg) was hydrogenated over prereduced 10% palladium oxide on carbon (50% aqueous paste 40 mg) in ethanol (20 ml) containing hydrochloric acid (0.6 mmol). After 1.5 h the catalyst was removed by filtration through hyflo and the filtrate was concentrated in vacuo. The residue was dissolved in EA (20 ml) and washed with 8% aqueous sodium bicarbonate and brine, dried (Na$_2$SO$_4$) and evaporated to an oil. Purification by FCC eluting with EA ME-TE (90:10:1) gave the title compound as a white powder (120 mg) m.p. 60°-63°. T.l.c. (EA-ME-TE 80:20:1) Rf 0.42.

(b) 4-Amino-3,5-dichloro-α-[[[5-(2-phenylethoxy)pentyl]amino]methyl]benzenemethanol, a cream solid (370 mg), m.p. 64°-65°, t.l.c. (EA-ME-TE 80:20:1) Rf 0.40 was similarly prepared from Example 1(c) (650 mg).

EXAMPLE 3

4-Amino-α-[[[6-[2-(4-aminophenyl)ethoxy]hexyl]amino]methyl]-3,5-dichlorobenzenemethanol Example 1(a) (300 mg) was hydrogenated over prereduced 10% palladium oxide on carbon (50% aqueous paste, 60 mg) in ethanol (20 ml) containing hydrochloric acid (1:9 conc. HCl/ethanol, 1 ml). The catalyst was removed by filtration through hyflo and the ethanol was removed under vacuum. 8% Aqueous sodium bicarbonate (20 ml) was added to the residue, which was then extracted with EA (2×20 ml). The organic extracts were washed with water and brine, dried (Na$_2$SO$_4$) and concentrated to a yellow oil which was purified by FCC eluting with EA-ME-TE (80:20:1) to give a solid. Trituration with ER gave the title compound as an off-white powder (160 mg) m.p. 71°-73°. T.l.c. (EA-ME-TE 80:20:1) Rf 0.32.

EXAMPLE 4

(a) 4-Amino-3,5-dichloro-α-[[[1-methyl-5-(2-phenylethoxy)pentyl]amino]methyl]benzenemethanol Example 1(e) (890 mg) was hydrogenated over prereduced 10% palladium oxide on carbon (50% aqueous paste, 100 mg) in ethanol (20 ml) containing hydrochloric acid (conc. HCl/ethanol, 1:9 v/v, 1.6 ml). The catalyst was removed by filtration through hyflo and the ethanol was evaporated. The residue was partitioned between 8% aqueous sodium bicarbonate and EA. The aqueous layer was re-extracted with EA and the combined organic extracts were washed with brine, dried (Na$_2$SO$_4$) and concentrated to give a yellow oil which was purified by FCC eluting with EA-TE (99:1) to yield the title compound as a colourless oil (580 mg). T.l.c. (EA-TE 99:1) Rf 0.16.

(b) 4-Amino-3,5-dichloro-α-[[[6-(4-phenylbutoxy)hexyl]amino]methyl]benzene methanol was similarly prepared from Example 1(d) (320 mg). Purification by FCC eluting with EA-ME-TE (80:20:1) followed by trituration with dry ER and drying in vacuo gave the title compound as a white powder (180 mg) m.p. 74°-76°. Found: C,63.38; H,7.59; N,6.06; Cl,15.47. C$_{24}$H$_{34}$Cl$_2$N$_2$O$_2$ requires C,63.57; H,7.56; N,6.18; Cl,15.64%.

EXAMPLE 5

4-Amino-3,5-dichloro-α-[[[1,1-dimethyl-5-[2-[4-(4-morpholinyl)phenyl]ethoxy]pentyl]amino]methyl]benzenemethanol (Z)-butenedioate (salt) 1:1

A solution of 4-amino-3,5-dichloro-α-oxobenzeneacetaldehyde (1.9 g) and Intermediate 12 (2.5 g) in benzene (50 ml) was refluxed in a Dean-Stark apparatus for 1 h. The solvent was evaporated, and the residual oil was dissolved in methanol (50 ml) cooled in an ice-bath and treated portionwise with sodium borohydride (1.5 g). The yellow mixture was stirred at room temperature overnight then concentrated to an oil which was partitioned between water (100 ml) and EA (100 ml). The organic layer was washed with water and brine, dried (Na$_2$SO$_4$) and concentrated to an oil which was purified by FCC eluting with T-ET-ammonia (80:20:1) to give a pale yellow oil (2.5 g). T.l.c. (T-ET-ammonia 80:20:1) Rf 0.53. A sample of the oil (150 mg) in methanol (2 ml) was treated with a solution of maleic acid (150 mg) in methanol (2 ml). The solvent was removed under vacuum and the residue was triturated with ER to give the title salt as a white powder (180 mg) m.p. 110°–115° (dec).

Analysis Found: C,57.28; H,6.71; N,6.32; Cl,10.83. $C_{27}H_{39}Cl_2N_3O_3 \cdot C_4H_4O_4 \cdot 1/2H_2O$ requires C,57.32; H,6.83; N,6.47; Cl,92%.

EXAMPLE 6

(a) 4-Amino-3,5-dichloro-α-[[[6-[2-[4-(4-morpholinyl)phenyl]ethoxy]hexyl]amino]methyl]benzenemethanol Example 1(g) (1.2 g) was hydrogenated over pre-reduced 10% palladium oxide on carbon (50% aqueous paste, 250 mg) in ethanol (25 ml) containing hydrochloric acid (conc. hydrochloric acid/ethanol 1:9 v/v, 2.0 ml). The catalyst was removed by filtration through hyflo, the ethanol was evaporated and the residue was partitioned between EA (50 ml) and 8% aqueous sodium bicarbonate (50 ml). The organic layer was washed with water and brine, dried ($Na_2SO_4$) and concentrated to a solid which was triturated with ER to give the title compound as an off-white powder (820 mg) m.p. 102°–103°.

Found: C,61.00; H,7.25; N,8.07; Cl,13.65. $C_{26}H_{37}Cl_2N_3O_3$ requires C,61.17; H,7.31; N,8.23; Cl,13.89%.

(b) N-[4-[2-[[6-[[2-(4-Amino-3,5-dichlorophenyl)-2-hydroxyethyl]amino]hexyl]oxy]ethyl]phenyl]acetamide (0.60 g) as a white solid m.p. 98°–100° was similarly prepared from Example 1(h) (1.08 g) using pre-reduced 10% palladium on charcoal (100 mg) as the catalyst.

Found: C,59.7; H,6.9; N,8.4; Cl,14.6 $C_{24}H_{33}Cl_2N_3O_3$ requires: C,59.8; H,6.9; N,8.7; Cl,14.7%

EXAMPLE 7

(a) 4-Amino-3,5-dichloro-α-[[[5-[2-[4-(methylphenyl)ethoxy]pentyl]amino]methyl]benzenemethanol Example 1(i) (0.92 g) was hydrogenated over pre-reduced 10% palladium on charcoal (100 mg) in ethanol (20 ml) containing hydrochloric acid (conc. hydrochloric acid/ethanol, 1:9 v/v, 1.62 ml) and the catalyst was removed by filtration (hyflo). The filtrate was concentrated and the residue was partitioned between EA (50 ml) and 8% aqueous sodium bicarbonate (2×50 ml). The organic layer was washed with brine (50 ml), dried ($Na_2SO_4$) and concentrated to give an oil (0.7 g) which was purified by FCC eluting with EA-TE (100:1) followed by trituration with ether to give the title compound as a white solid (0.46 g) m.p. 78°–79°.

Found: C,62.2; H,6.9; N,6.5; Cl,16.8. $C_{22}H_{30}Cl_2N_2O_2$ requires C,62.1; H,7.1; N,6.6; Cl,16.07%.

(b) 4-Amino-3,5-dichloro-α-[[[5-[3-(4-methoxyphenyl)propoxy]pentyl]amino]methyl]benzenemethanol was similarly prepared from Example 1(k) (450 mg) using pre-reduced 10% palladium oxide on carbon (50% aqueous paste, 100 mg) as the catalyst. Purification by FCC eluting with T-ET-TE (90:10:1) followed by trituration with dry ER gave the title compound as a white solid (150 mg) m.p. 63°–64°. Found: C,60.30; H,7.13; N,6.03; Cl,15.74. $C_{23}H_{32}Cl_2N_2O_3$ requires C,60.66; H,7.08; N,6.15; Cl,15.57%.

(c) 4-Amino-3,5-dichloro-α-[[[5-[2-(4-fluorophenyl)ethoxy]pentyl]amino]methyl]benzenemethanol was similarly prepared from Example 1(f) (0.783 g) using 10% palladium on charcoal (100 mg) as the catalyst. Final trituration with hexane gave the title compound as a white solid (0.225 g) m.p. 75°–76°.

Analysis Found: C,59.0; H,6.5; N,6.5; Cl,16.4. $C_{21}H_{27}Cl_2FN_2O_2$ requires C,58.8; H,6.3; N,6.5; Cl,16.5%.

EXAMPLE 8

[3-[[5-[[2-(4-Amino-3,5-dichlorophenyl)-2-hydroxyethyl]amino]pentyl]oxy]propyl]-1,3-benzenediol Example 1(j) (2.20 g) was hydrogenated over pre-reduced 10% palladium oxide on charcoal (200 mg) in ethanol (30 ml) containing hydrochloric acid (conc. HCl/ET 1:9 v/v 2.75 ml). The catalyst was removed by filtration (hyflo). The filtrate was concentrated and the residue was partitioned between EA (50 ml) and 8% aqueous sodium bicarbonate (2×50 ml). The organic layer was washed with brine (50 ml) dried ($Na_2SO_4$) and concentrated to give an oil (1.05 g) which was purified by FCC eluting with EA-ME-TE (90:10:1) to give the title compound as a white foam (0.369 g). T.l.c. (EA-ME-TE 90:10:1) Rf 0.2. Found: C,57.4; H,6.7; N,5.9; Cl,15.1 $C_{22}H_{30}Cl_2N_2O_4$ requires C,57.8; H,6.6; N,6.1; Cl,15.5%.

EXAMPLE 9

4-Amino-3,5-dichloro-α-[[[5-(2-phenylethoxy)-3-pentynyl]amino]methyl]benzenemethanol Intermediate 3 (802 mg) in DMF (2 ml) was added to a stirred solution of 4-amino-α-(aminomethyl)-3,5-dichlorobenzenemethanol (1.0 g) and N,N-diisopropylethylamine (650 mg) in DMF (20 ml) at 100° under nitrogen. After 2 h the solvent was evaporated and the residue was purified by FCC twice eluting with T-ET-TE (9:5:1) to give a pale yellow oil which was triturated with H to give the title compound as a white solid (80 mg) m.p. 62.5°–63°. Found: C,61.39; H,5.93; N,6.79; Cl,17.37. $C_{21}H_{24}Cl_2N_2O_2$ requires C,61.92; H,5.94; N,6.88; Cl,17.41%.

EXAMPLE 10

4-Amino-3,5-dichloro-α-[[[5-[2-(4-methoxyphenyl)ethoxy]pentyl]amino]methyl]benzenemethanol hydrochloride Example 1(l) (230 mg) was hydrogenated over 10% palladium oxide on carbon (50% aqueous paste, 40 mg) in ethanol (10 ml). The catalyst was removed by filtration through hyflo and the ethanol was evaporated to give a green solid which was triturated with dry ether to give the title compound as a pale green powder (170 mg) m.p. 134°–137° (dec).

Analysis Found: C,54.28; H,6.45; N,5.58; Cl,21.35. $C_{22}H_{30}Cl_2N_2O_3 \cdot HCl \cdot \frac{1}{2}H_2O$ requires C,54.27; H,6.62; N,5.75; Cl,21.85%.

EXAMPLE 11

Ethyl 4-[3-[[6-[[(4-amino-3,5-dichlorophenyl)2-hydroxyethyl]amino]hexyl]oxy]propyl]benzoate Intermediate 18 (500 mg) in ET (20 ml) containing hydrochloric acid (concHCl 1:9 v/v, 0.76 ml) was hydrogenated over pre-reduced 10% palladium on charcoal (50% paste in water, 60 mg). The reaction mixture was filtered (hyflo) and the filtrate was concentrated. The residue was partitioned between EA (50 ml) and 8% aqueous sodium bicarbonate (2×50 ml). The organic layer washed with brine (50 ml), dried (Na$_2$SO$_4$) and concentrated. The residue was purified by FCC eluting with EA-H-TE (50:50:1) to give the title compound as a white solid (97 mg) m.p. 66°-68°. T.l.c. (EA-H-TE 50:50:1) Rf 0.05.

EXAMPLE 12

4-Amino-3,5-dichloro-α-[[[6-[3-[4-(hydroxymethyl)-phenyl]propoxy]hexyl]amino]methyl]benzenemethanol The compound of Example 11 (88 mg) in ER (4 ml) was added dropwise to a stirred suspension of lithium aluminium hydride (50 mg) in ER (4 ml) under nitrogen. The reaction mixture was stirred for 2.5 h at room temperature and treated dropwise with water (0.05 ml), 2N aqueous sodium sodium hydroxide (0.1 ml) and water (0.1 ml). The mixture was filtered (hyflo) and the filtrate was concentrated to give a colourless oil (64 mg), which on trituration with ER afforded the title compound as a white solid m.p. 56°-59°. T.l.c. (T-ET-NH$_3$ 39:11:1) Rf 0.44.

EXAMPLE 13

4-[3-[[6-[[2-(4-Amino-3,5-dichlorophenyl)-2-hydroxyethyl]amino]hexyl]oxy]propyl]benzamide Intermediate 30 (1.3 g) was hydrogenated over 10% palladium oxide on carbon (50% aqueous paste, 280 mg) in ethanol (15 ml) containing hydrochloric acid (conc. HCl/EtOH, 1:9 v/v, 2 ml). The catalyst was removed by filtration through hyflo, the solvent was evaporated and the residue was partitioned between 8% sodium bicarbonate (25 ml) and ethyl acetate (25 ml). The aqueous layer was re-extracted with ethyl acetate (25 ml) and the combined organic extracts were washed with 8% sodium bicarbonate and brine, dried and concentrated to a semi-solid which was triturated with ether/ethyl acetate (~4:1) to give the title compound as an off-white solid (240 mg, 22%) m.p. 91°-94°, t.l.c. (System A 80:20:2) Rf 0.25.

Examples 14–21 were prepared in a similar manner:

EXAMPLE 14

N-[4-[3-[[6-[[2-(4-Amino-3,5-dichlorophenyl)-2-hydroxyethyl]amino]hexyl]oxy]propyl]phenyl]methanesulphonamide From Intermediate 20 (500 mg). Evaporation of the ethyl acetate extracts gave an oil which was purified by FCC eluting with System B (95:5:1) followed by trituration with dry ether to give the title compound as a white powder (100 mg) m.p. 62°-64°.

Analaysis Found: C,54.82; H,7.26; N,7.36. C$_{24}$H$_{35}$Cl$_2$N$_3$O$_4$S.0.35C$_4$H$_{10}$O requires C,54.63; H,6.95; N,7.52%.

EXAMPLE 15

Ethyl 4-[3-[[6-[[(4-amino-3,5-dichlorophenyl)-2-hydroxyethyl]aminohexyl]oxy]propyl]benzoate From ethyl 4-[3-[[6-[[(4-amino-3,5-dichlorophenyl)-2-hydroxyethyl]-(phenylmethyl)amino]hexyl]oxy]1-propynyl]benzoate (500 mg), using pre-reduced 10% palladium on charcoal (50% paste in water, 60 mg) as the catalyst for hydrogenation. The residue obtained by evaporation of the ethyl acetate extract was purified by FCC eluting with System C (50:50:1) to give the title compound as a white soluid (97 mg) m.p. 66°-68°. T.l.c. (System C 50:50:1) Rf 0.05.

EXAMPLE 16

N-[4-[3-[[6-[[2-(4-Amino-3,5-dichlorophenyl)-2-hydroxyethyl]amino]hexyl]oxy]propyl]phenyl]-2-(dimethylamino)acetamide, (E)-butenedioate (salt) (1:1)

From Intermediate 31 (750 mg), using conc. HCl/EtOH, 1:9 v/v, 2.2 m. The yellow oil (520 mg) obtained after concentration of the ethyl acetate extracts was dissolved in methanol (5 ml) and treated with a solution of fumaric acid (120 mg) in methanol (2 ml), the methanol was evaporated and the residue was triturated with ether to give a yellow solid (610 mg) which was recrystallised from isopropanol (15 ml) to give the title compound as a white solid (100 mg) m.p. 106°-110°.

Analyis Found: C,56.32; H,6.97; N,7.94; Cl,11.32. C$_{27}$H$_{40}$Cl$_2$N$_4$O$_3$.C$_4$H$_4$O$_4$ requires C, 56.79; H,6.76; N,8.55; Cl, 10.82%.

EXAMPLE 17

4-[3-[[6-[[2-(4-Amino-3,5-dichlorophenyl)-2-hydroxyethyl]amino]hexyl]oxy]propyl]-N,N-dimethylbenzamide, (E)-butenedioate (salt) (2:1)

From Intermediate 39 (0.82 g) using pre-reduced 10% palladium on charcoal (50% aqueous paste, 100 mg) as the catalyst for hydrogenation. Evaporation of the ethyl acetate extracts gave an oil which was purified by FCC eluting with System B (95:5:1) to give an oil. The oil (0.42 g) in methanol (2 ml) was treated with (E)-butenedioic acid (47.6 mg) in methanol (2 ml) and the solution was concentrated. The residue was triturated with diethyl ether to give the title compound as a white solid (0.47 g) m.p. 107°-109°.

Analysis Found: C,59.0; H,7.2; N,7.2; Cl,12.6. C$_{26}$H$_{37}$Cl$_2$N$_3$O$_3$.0.5C$_4$H$_4$O$_4$ requires C,59.2; H,6.9; N,7.4; Cl,12.5%.

EXAMPLE 18

4-[4-[3-[[6-[[2-(4-Amino-3,5-dichlorophenyl)-2-hydroxyethyl]amino]hexyl]oxy]propyl]benzoyl]morpholine From Intermediate 40 (0.70 g) using pre-reduced 10% palladium on charcoal (50% aqueous paste, 80 mg) at the catalyst for hydrogenation. Evaporation of the ethyl acetate extract gave an oil which was purified by FCC eluting with System B (95:5:1) to give the title compound as a yellow oil (391 mg). A solution of the title compound (390 mg) in methanol (2 ml) was treated with (E)-butenedioic acid (41.1 mg) in methanol (2 ml), and the solvent was evaporated to give an oil which, on trituration with diethyl ether, gave the (E)-butenedioate salt (2:1) of the title compound as a white solid (40 mg), m.p. 114°-116°.

Analysis Found: C,58.7; H,6.0; N,6.7; Cl,11.9. (C$_{28}$H$_{39}$Cl$_2$N$_3$O$_4$)$_2$.C$_4$H$_4$O$_4$ requires C,59.0; H,6.8; N,6.9; Cl,11.6%.

EXAMPLE 19

N-[[3-[3-[[6-[[2-(4-Amino-3,5-dichlorophenyl)-2-hydroxyethyl]amino]hexyl]oxy]propyl]phenyl]methyl]acetamide From intermediate 34 (1.40 g) using pre-reduced 10% palladium on charcoal (50% aqueous paste, 170 mg) as the catalyst for hydrogenation. The solid obtained from the ethyl acetate extracts was triturated with diethyl ether to give the title compound as a white solid (0.76 g) m.p. 91°-94°, t.l.c. (System A 80:20:2) Rf 0.45.

Analysis Found: C,60.7; H,7.5; N,7.9; Cl,13.9. $C_{26}H_{37}Cl_2N_3O_3$ requires C,61.2; H,7.3; N,8.2; Cl,13.9%.

EXAMPLE 20

2-[4-[3-[[6-[[2-(4-Amino-3,5-dichlorophenyl)-2-hydroxyethyl]amino]hexyl]oxy] propyl]phenoxy], N,N-dimethylacetamide (E)-butenedioate (salt) (2:1)

From Intermediate 36 (0.99 g) using pre-reduced 10% palladium on charcoal (50% aqueous paste, 115 mg) as the catalyst for hydrogenation. Concentration of the ethyl acetate extract gave an oil. The oil (0.70 g) in methanol (2 ml) was treated with (E)-butenedioic acid (75.5 mg) in methanol (2 ml) and the solution was concentrated. The residue was triturated with diethyl ether to give the title compound as a buff solid (0.63 g), m.p. 116°-118°, t.l.c. (System B 95:5:1) Rf 0.17.

EXAMPLE 21

N-[4-[3-[[6-[[2-(4-Amino-3,5-dichlorophenyl)-2-hydroxyethyl]amino]hexyl]oxy]propyl]phenyl]-N-methylmethanesulphonamide hydrochloride From Intermediate 38 (250 mg) using pre-reduced 10% palladium oxide on carbon (50% aqueous paste, 50 mg) as the catalyst for hydrogenation. Concentration of the ethyl acetate extract gave an oil which was purified by FCC eluting with System B (99:1:1→95:5:1) to give a yellow oil (130 mg). The oil in ether (5 ml) was treated with ethereal hydrogen chloride and the resultant oil was triturated with dry ether to give the title compound as a yellow solid (90 mg), t.l.c. (System B 95:5:1) Rf 0.56.

Analysis Found: C,51.14; H, 7.02; N, 6.87; Cl,17.82; S,5.00. $C_{25}H_{37}Cl_2N_3O_4S.HCl$ requires C,51.50; H,6.57; N,7.21; Cl,18.24; S,5.50%.

EXAMPLE 22

4-Amino-3,5-dichloro-α-[[[6-[3-[4-[2-(dimethylamino)ethyl]phenyl]propoxy]hexyl]amino]methyl]benzenemethanol A solution of Intermediate 21 as its free base (1.54 g), Intermediate 41 (2.94 g), BTPC (100 mg) and copper (I) iodide (10 mg) in diethylamine (30 ml) and acetonitrile (10 ml) was stirred under nitrogen for 18 h. The solution was concentrated in vacuo to give a brown oil which was purified by FCC eluting with System B (95:5:1) to give a yellow oil (2.4 g). The oil (2.3 g) was hydrogenated over 10% palladium oxide on carbon (50% aqueous paste, 500 mg) in ethanol (20 ml) containing hydrochloric acid (conc. HCl/EtOH; 1:9 v/v, 6.9 ml). The catalyst was removed by filtration through hyflo, the ethanol was evaporated and the residue was partitioned between 8% sodium bicarbonate (20 ml) and ethyl acetate (20 ml). The aqueous layer was re-extracted with ethyl acetate (20 ml) and the combined organic extracts were washed with sodium bicarbonate (20 ml) and brine (20 ml), dried and concentrated to give a yellow oil. The oil was purified by FCC eluting with System B (98:2:1) to give a pale yellow oil (1.2 g) which was triturated with hexane to give the title compound as a white solid (1.1 g) m.p. 41.5-43.5.

Analysis Found: C,63.23; H,8.37; N,8.10; Cl,13.69. $C_{27}H_{40}Cl_2N_3O_2$ requires C,63.64; H,7.91; N,8.25; Cl,13.92%.

EXAMPLE 23

4-[4-[5-[[2-(4-Amino-3,5-dichlorophenyl)-2-hydroxyethyl]amino]pentyloxy]butyl]-N,N-dimethylbenzeneacetamide Intermediate 35 (1.00 g) in ethanol (20 ml) containing hydrochloric acid (conc. HCl/EtOH, 1:9 v/v, 1.48 ml) was hydrogenated over pre-reduced 10% palladium on charcoal (150 mg, 50% paste in water). The reaction mixture was filtered (hyflo) and the filtrate was concentrated. The residue was partitioned between ethyl acetate (100 ml) and 8% aqueous sodium bicarbonate (2×50 ml). The dried organic layer was concentrated and the residual oil was purified by FCC eluting with System D (100:0:1→90:10:1) to give the title compound as a yellow oil (0.69 g). The title compound (469 mg) in methanol (2 ml) was treated with (E)-butenedioic acid (51.9 mg) in methanol (2 ml). The solution was concentrated to give an oil which was triturated with diethyl ether to give the (E)-butenedioate salt (2:1) of the title compound (407 mg), m.p. 107°-110°.

Analysis Found: C,59.9; H,7.4; N,7.0; Cl,12.0 $C_{27}H_{39}Cl_2N_3O_3.0.5C_4H_4O_4$ requires C,59.8; H,7.1; N,7.2; Cl,12.2%.

EXAMPLE 24

N-[4-[3-[[6-[[2-(4-Amino-3,5-dichlorophenyl)-2-hydroxyethyl]amino]hexyl]oxy]ethyl]phenyl]methanesulphonamide Intermediate 37 (1.2 g) was hydrogenated as in Example 23, using pre-reduced 10% palladium oxide on carbon (50% aqueous paste, 150 mg) as the catalyst. Evaporation of the ethyl acetate extract gave a yellow oil which was purified by FCC eluting with System B (92:8:1) to give a pale yellow oil which when triturated with ether gave the title compound as a white solid (445 mg), m.p. 62°-65°.

Analysis Found: C,52.94; H,6.40; N,7.79; Cl,13.96; S,6.17. $C_{23}H_{33}Cl_2N_3O_4S$ requires C,53.28; H,6.42; N,8.10; Cl,13.68; S,6.18%;

EXAMPLE 25

4-[3-[[6-[[2-(4-Amino-3,5-dichlorophenyl)-2-hydroxyethyl]amino]hexyl]oxy]propyl]benzeneacetamide 4-[3-[(6-Bromohexyl)oxy]propyl]benzeneacetamide (950 mg) was added to a stirred solution of 4-amino-α-(aminomethyl)-3,5-dichloro- benzenemethanol (900 mg) and DEA (650 mg) in DMF (10 ml) at 100° under nitrogen. After 1 h the solvent was evaporated and the residue was partitioned between 8% sodium bicarbonate (20 ml) and ethyl acetate (20 ml). The organic layer was washed with water and brine, dried and concentrated in vacuo to give a yellow solid which was triturated with ether to give the title compound as an off-white powder (510 mg) m.p. 104°-106°.

Analysis Found: C,60.58; H,7.35; N,8.11; Cl,13.83. $C_{25}H_{35}Cl_2N_3O_3$ requires C,60.48; H,7.11; N,8.46; Cl,14.28%.

EXAMPLE 26

4-Amino-3,5-dichloro-α-[[[6-[3-[4-(methoxymethyl)phenyl]propoxy]hexyl]amino]methyl]benzenemethanol, (E)-butenedioate (2:1) (salt)

1-[3-[(6-Bromohexyl)oxy]propyl]-4-(methoxymethyl)benzene (1.0 g) and 4-amino-α-(aminomethyl)-3,5-dichlorobenzenemethanol (1.0 g) were reacted according to the method of Example 25. Concentration of the ethyl acetate extract gave an oil which was purified by FCC eluting with System B (90:10:1) to give a yellow oil (620 mg). The oil in isopropanol (5 ml) was treated with a hot solution of fumaric acid (20 mg) in isopropanol (2 ml) and after 1 h the two phase system was stirred vigorously to leave a palte yellow precipitate which was collected by filtration and dried in vacuo to give the title compound as a pale yellow powder (550 mg) m.p. 110°–112°, t.l.c. (System A 80:20:2) Rf 0.43.

Analysis found: C,59.33; H.6.87; N,4.88; Cl,13.31. $C_{25}H_{36}Cl_2N_2O_3.0.5C_4H_4O_4$ requires C,59.89; H,7.07; N,5.17; Cl,13.09%.

EXAMPLE 27

4-[3-[[6-[[2-(4-Amino-3,5-dichlorophenyl)-2-hydroxyethyl]amino]hexyl]oxy]propyl]benzoic acid

The product according to Example 15 (600 mg) in ethanol (8 ml) was treated with 2N sodium hydroxide (4 ml) and stirred at reflux for 1 h. The ethanol was evaporated, water (20 ml) was added to the residue and the mixture was neutralised using 2N hydrochloric acid. Ethyl acetate (25 ml) was added and the two phase mixture was vigorously stirred for 10 min. The resulting precipitate was collected by filtration, washed with ethyl acetate and dried to give a cream solid (450 mg), which was triturated with warm methanol (10 ml) and filtered to give the title compound as a white powder (290 mg) m.p. 190°–191°.

Analysis Found: C,59.22, H6.82; N,5.62; Cl,14.40. $C_{24}H_{32}Cl_2N_2O_4$ requires C,59.63; H6.67; N,5.79; Cl,14.67%.

EXAMPLE 28

4-Amino-3,5-dichloro-α-[[[6-[3-[4-[(4-morpholinyl)methyl]phenyl]propoxy]hexyl]amino]methyl]benzenemethanol

The product according to Example 18 (0.67 g) in benzene (10 ml) was added dropwise to lithium aluminium hydride (300 mg) in dry diethyl ether (15 ml) at room temperature under nitrogen. The suspension was stirred for 18 h at room temperature and treatment with water (0.3 ml), 2N aqueous sodium hydroxide (0.6 ml) and water (0.6 ml) gave a precipitate which was filtered off (hyflo). The filtrate was concentrated to give an oil which was purified by FCC eluting with System B (95:5:1) to give the title compound as a white solid (318 mg) m.p. 57°–59°, t.l.c. (System B 95:5:1) Rf 0.22.

EXAMPLE 29

4-Amino-3,5-dichloro-α-[[[6-[3-[-4[[2-(dimethylamino)ethyl]amino]phenyl]propoxy]hexyl]amino]-methyl]benzenemethanol-(E)-butenedioate (2:3) (salt)

The product according to Example 16 as its free base (440 mg) was treated with lithium aluminium hydride (420 mg) following the method of Example 28. After 7 days, water (1 ml), 2N aqueous sodium hydroxide (2 ml) and water (1 ml) were added successively, the precipitate being removed by filtration through hyflo and the ether was evaporated to leave a brown oil. A solution of the oil (320 mg) and fumaric acid (78 mg) in methanol (3 ml) was concentrated to an oil which was triturated with ether to give the title compound as a brown solid (230 mg), m.p. 41°–45°.

Analysis Found: C,56.59; H,7.35; N,7.30; Cl,9.61. $C_{27}H_{42}Cl_2N_4O_2.1.5C_4H_4O_4$ requires C,56.66; H,6.91; N,8.01; Cl,10.13%.

Examples 30 and 31 were prepared according to the method of Example 13:

EXAMPLE 30

4-Amino-3,5-dichloro-α-[[[6-[3-[4-[bis(2-hydroxyethyl)amino]phenyl)propoxy]hexyl]amino]methyl]benzenemethanol

From Intermediate 43 (402 mg), using conc. HCl/EtOH 1:9 v/v, 0.9 ml. Evaporation of the ethyl acetate extracts gave a brown oil which was purified by FCC eluting with System B (95:5:1→80:20:1) to give the title compound as a pale yellow oil (85 mg), t.l.c. (System A 80:20:2) Rf. 0.33. δ (CDCl$_3$) 1.2–1.63 and 1.84 (—CH$_2$—), 3.4 (—OCH$_2$—); 3.54 and 3.81, 8H, (—CH$_2$CH$_2$OH)$_2$, 6.62 and 7.04, 4H, (CH of phenyl ring), 7.17, 2H, (CH of dichloroaniline ring).

EXAMPLE 31

4-Amino-3,5-dichloro-α-[[[6-[3-[4-[2-(dimethylamino)ethoxy]phenyl]propoxy)hexyl]amino]methyl]benzenemethanol

From Intermediate 44 (3.42 g), using pre-reduced 10% palladium on charcoal (50% paste in water, 750 mg) as the catalyst for hydrogenation, in ethanol (30 ml) containing hydrochloric acid (conc. HCl/EtOH 1:9 v/v, 10.1 ml). The oil obtained by evaporation of the ethyl acetate extracts was purified by FCC eluting with System A (80:20:2) followed by further FCC chromatography of the impure fractions eluting with System B (95:5:1). The combined oils obtained (493 mg) in methanol (5 ml) were treated with (E)-butenedioic acid (109 mg) in methanol (5 ml). The solution was concentrated and the residual foam was triturated with diethyl ether to give the title compound as a pale yellow foam (0.361 g), t.l.c. (System A 80:20:2) Rf 0.5.

Analysis Found C,56.1; H,7.2; N,6.2; Cl,11.0 $C_{27}H_{41}Cl_2N_3O_3.1.25C_4H_4O_4.0.8H_2O$ requires C,56.0; H,7.0; N,6.1; Cl,10.3%.

The following are examples of suitable formulations of compounds of the invention. The term "active ingredient" is used herein to represent a compound of the invention.

| Tablets (Direct Compression) | |
|---|---|
| | mg/tablet |
| Active ingredient | 2.0 |
| Microcrystalline Cellulose USP | 196.5 |
| Magnesium Stearate BP | 1.5 |
| Compression weight | 200.0 |

The active ingredient is sieved through a suitable sieve, blended with the excipients and compressed using 7 mm diameter punches.

Tablets of other strengths may be prepared by altering the ratio of active ingredient to microcrystalline cellulose or the compression weight and using punches to suit.

The tablets may be film coated with suitable film forming materials, such as hydroxypropylmethylcellulose, using standard techniques. Alternatively the tablets may be sugar coated.

| Syrup (Sucrose-free) | |
| --- | --- |
| | mg/5 ml dose |
| Active ingredient | 2.0 mg |
| Hydroxypropyl methylcellulose USP (viscosity type 4000) | 22.5 mg |
| Buffer | |
| Flavour | |
| Colour | as required |
| Preservative | |
| Sweetener | |
| Purified Water BP to | 5.0 ml |

The hydroxypropyl methylcellulose is dispersed in hot water, cooled and then mixed with an aqueous solution containing the active ingredient and the other components of the formulation. The resultant solution is adjusted to volume and mixed. The syrup is clarified by filtration.

METERED DOSE PRESSURISED AEROSOL

| A. Suspension Aerosol | | |
| --- | --- | --- |
| | mg/metered dose | Per can |
| Active ingredient micronised | 0.100 | 26.40 mg |
| Oleic Acid BP | 0.100 | 2.64 mg |
| Trichlorofluoromethane BP | 23.64 | 5.67 g |
| Dichlorodifluoromethane BP | 61.25 | 14.70 g |

The active ingredient is micronised in a fluid energy mill to a fine particle size range. The Oleic Acid is mixed with the Trichlorofluoromethane at a temperature of 10°–15° C. and the micronised drug is mixed into the solution with a high shear mixer. The suspension is metered into aluminium aerosol cans and suitable metering valves delivering 85 mg of suspension are crimped onto the cans and the Dichlorodifluoromethane is pressure filled into the cans through the valves.

| B. Solution Aerosol | | |
| --- | --- | --- |
| | mg/metered dose | Per can |
| Active ingredient | 0.055 | 13.20 mg |
| Ethanol BP | 11.100 | 2.66 g |
| Dichlorotetrafluoroethane BP | 25.160 | 6.04 g |
| Dichlorodifluoromethane BP | 37.740 | 9.06 g |

Oleic acid BP, or a suitable surfactant e.g. Span 85 (sorbitan trioleate) may also be included.

The active ingredient is dissolved in the ethanol together with the oleic acid or surfactant if used. The alcoholic solution is metered into suitable aerosol containers followed by the dichlorotetrafluoroethane. Suitable metering values are crimped onto the containers and dichlorodifluoromethane is pressure filled into them through the valves.

| Injection for Intravenous Administration | |
| --- | --- |
| | mg/ml |
| Active ingredient | 0.5 mg |
| Sodium Chloride BP | as required |
| Water for Injection BP to | 1.0 ml |

Sodium chloride may be added to adjust the tonicity of the solution and the pH may be adjusted, using acid or alkali, to that of optimum stability and/or facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

| Inhalation Cartridges | |
| --- | --- |
| | mg/cartridge |
| Active ingredient micronised | 0.200 |
| Lactose BP to | 25.0 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents of the cartridges are administered using a powder inhaler such as the Glaxo Rotahaler.

We claim:

1. A compound of formula (I)

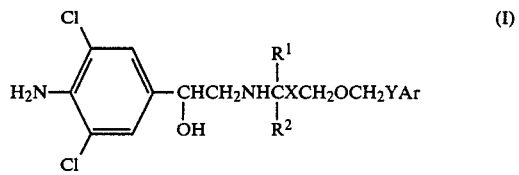

wherein $R^1$ and $R^2$ each represent a hydrogen atom or a $C_{1-3}$ alkyl group with the proviso that the sum total of carbon atoms in $R^1$ and $R^2$ is not more than 4;

X represents a $C_{1-6}$ alkylene, $C_{2-6}$ alkenylene or $C_{2-6}$ alkynylene chain;

Y represents a bond, or a $C_{1-4}$ alkylene, $C_{2-4}$ alkenylene or $C_{2-4}$ alknylene chain with the proviso that the sum total of carbon atoms in X and Y is not more than 8;

Ar represents a phenyl group substituted by a group —$NR^5COR^6$, where $R^5$ represents a hydrogen atom or a $C_{1-4}$alkyl group and $R^6$ represents a hydrogen atom or a $C_{1-4}$alkyl, $C_{1-4}$alkoxy or —$NR^3R^4$ group where $R^3$ and $R^4$ each represent a hydrogen atom, or a $C_{1-4}$alkyl group or Ar is a phenyl group substituted by a group —$(CH_2)_rR^7$ where r is 0 or 1 and $R^7$ is —$COR^9$ where $R^9$ represents hydroxy, $C_{1-4}$alkoxy or a group —$NR^3R^4$;

and their physiologically acceptable salts and solvates thereof.

2. A compound according to claim 1, in which the chain X is —$CH_2$—, —$(CH_2)_2$—, —$(CH_2)_3$—, —$(CH_2)_4$—, —$(CH_2)_5$—, —$(CH_2)_6$—, —$CH_2C\equiv C$—, —$(CH_2)_2CH=CH$—, —$(CH_2)_2C\equiv C$—, —$CH=CHCH_2$—, —$CH=CH(CH_2)_2$— or —$CH_2C\equiv CCH_2$— and the chain Y is a bond, —$CH_2$—, —$(CH_2)_2$—, —$(CH_2)_3$—, —$(CH_2)_4$—, —$CH=CH$—, —$C\equiv C$—, —$CH_2CH=CH$—, or —$CH_2C\equiv C$—.

3. A compound according to claim 1, in which X is a $C_{2-6}$ alkylene or $C_{2-6}$ alkynylene chain and Y is a $C_{1-4}$ alkylene chain.

4. A compound according to claim 1, in which $R^1$ and $R^2$ independently represent a hydrogen atom or a methyl group.

5. A compound according to claim 1, in which $R^1$ and $R^2$ are both hydrogen atoms or $R^1$ is a hydrogen atom and $R^2$ is a $C_{1-3}$ alkyl group.

6. A pharmaceutical composition for therapy or prophylaxis of a disease associated with reversible airways obstruction such as asthma or chronic bronchitis, which comprises an effective amount to alleviate said disease of at least one compound of general formula (I) as defined in claim 1 or a physiologically acceptable salt or solvate thereof, together with a physiologically acceptable carrier or excipient.

7. A pharmaceutical composition for the treatment of premature labour, depression, congestive heart failure, an inflammatory or allergic skin disease, glaucoma or a condition in which there is an advantage in lowering gastric acidity such as gastric or peptic ulceration, which comprises an effective amount to alleviate said condition of at least one compound of general formula (I) as defined in claim 1 or a physiologically acceptable salt or solvate thereof, together with a physiologically acceptable carrier or diluent.

8. A compound selected from ethyl 4-[3[[6-[[4-amino-3,5-dichlorophenyl)-2-hydroxyethyl]aminohexyl]oxy]propyl]benzoate;

4-[3-[[6-[[2-(4-amino-3,5-dichlorophenyl)-2-hydroxyethyl]amino]hexyl]oxy]propyl]benzeneacetamide;

methyl 4-[3-[[6-[[2-(4-amino-3,5-dichlorophenyl)-2-hydroxyethyl]amino]hexyl]oxy]propyl]benzeneacetate;

N-[4-[2-[[6-[[2-(4-amino-3,5-dichlorophenyl)-2-hydroxyethyl]amino]hexyl]oxy]ethyl]phenyl]acetamide;

and physiologically acceptable salts and solvates thereof.

* * * * *